United States Patent
Chappa

(10) Patent No.: US 10,596,355 B2
(45) Date of Patent: Mar. 24, 2020

(54) CATHETER ASSEMBLY

(75) Inventor: Ralph A. Chappa, Ham Lake, MN (US)

(73) Assignee: Surmodics, Inc., Eden Prairie, MN (US)

( * ) Notice: Subject to any disclaimer, the term of this patent is extended or adjusted under 35 U.S.C. 154(b) by 692 days.

(21) Appl. No.: 13/173,164

(22) Filed: Jun. 30, 2011

(65) Prior Publication Data

US 2012/0004605 A1    Jan. 5, 2012

Related U.S. Application Data

(60) Provisional application No. 61/360,354, filed on Jun. 30, 2010.

(51) Int. Cl.
  *A61M 25/10*    (2013.01)

(52) U.S. Cl.
  CPC ...... *A61M 25/1034* (2013.01); *A61M 25/104* (2013.01); *A61M 2025/105* (2013.01); *A61M 2025/1031* (2013.01); *A61M 2025/1075* (2013.01); *A61M 2025/1086* (2013.01); *A61M 2025/1093* (2013.01)

(58) Field of Classification Search
  CPC .. A61M 2025/1081; A61M 2025/1084; A61M 2025/1086
  USPC ........... 604/96.01; 623/1.42, 1.43, 1.46, 1.39
  See application file for complete search history.

(56) References Cited

U.S. PATENT DOCUMENTS

| | | |
|---|---|---|
| 5,334,168 A | 8/1994 | Hemmer |
| 5,414,075 A | 5/1995 | Swan et al. |
| 5,634,901 A | 6/1997 | Alba et al. |
| 5,653,689 A | 8/1997 | Buelna et al. |
| 5,662,960 A * | 9/1997 | Hostettler ............. A61L 29/085 427/2.28 |
| 5,730,698 A | 3/1998 | Fischell et al. |

(Continued)

FOREIGN PATENT DOCUMENTS

| | | |
|---|---|---|
| WO | WO 99/59649 | 11/1999 |
| WO | WO 03/041760 A2 | 5/2003 |

(Continued)

OTHER PUBLICATIONS

U.S. Appl. No. 13/173,143, filed Jun. 30, 2011 entitled "Lipid Coating for Medical Devices Delivering Bioactive Agent".

(Continued)

*Primary Examiner* — Matthew F DeSanto
(74) *Attorney, Agent, or Firm* — Kagan Binder, PLLC

(57) ABSTRACT

A catheter assembly includes an expandable and collapsible structure having an outer surface. The expandable and collapsible structure is adapted to expand between a contracted state and a dilated state. A coating is disposed on the outer surface of the expandable and collapsible structure. The coating includes a bioactive agent. A sleeve is disposed over the coating. The sleeve is adapted to expand between a compressed state and an enlarged state and to return to the compressed state. The sleeve defines a plurality of openings in the compressed state. An outer diameter of the coating is less than an outer diameter of the sleeve when the expandable and collapsible structure is in the contracted state and greater than the outer diameter of the sleeve when the expandable and collapsible structure is in the dilated state.

3 Claims, 16 Drawing Sheets

(56) References Cited

U.S. PATENT DOCUMENTS

| | | |
|---|---|---|
| 6,007,833 A | 12/1999 | Chudzik et al. |
| 6,245,040 B1 | 6/2001 | Inderbitzen et al. |
| 6,278,018 B1 | 8/2001 | Swan |
| 6,280,414 B1 | 8/2001 | Shah et al. |
| 6,450,989 B2 | 9/2002 | Dubrul et al. |
| 6,544,579 B1 | 4/2003 | Landon |
| 6,703,040 B2 | 3/2004 | Katsarava et al. |
| 6,733,513 B2 | 5/2004 | Boyle et al. |
| 7,232,432 B2 | 6/2007 | Fulton, III et al. |
| RE40,359 E | 6/2008 | Katsarava et al. |
| 7,431,732 B2 | 10/2008 | Moriuchi et al. |
| 8,226,603 B2 * | 7/2012 | Von Oepen ............. A61F 2/958 604/101.01 |
| 2004/0243158 A1 * | 12/2004 | Konstantino .. A61B 17/320725 606/159 |
| 2005/0182361 A1 * | 8/2005 | Lennox ................ A61L 29/085 604/103.01 |
| 2005/0246009 A1 * | 11/2005 | Toner et al. ................. 623/1.11 |
| 2006/0030669 A1 | 2/2006 | Taton et al. |
| 2006/0259062 A1 | 11/2006 | Konstantino |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0255509 A1 * | 10/2008 | Wang ....................... 604/103.02 |
| 2009/0105687 A1 | 4/2009 | Deckman et al. |
| 2009/0246252 A1 * | 10/2009 | Arps ..................... A61L 29/085 424/425 |
| 2009/0254063 A1 * | 10/2009 | Oepen .............. A61M 25/1006 604/509 |
| 2010/0121371 A1 * | 5/2010 | Brooks et al. ................ 606/192 |
| 2010/0121372 A1 * | 5/2010 | Farnan ...................... A61F 2/86 606/194 |
| 2012/0059401 A1 * | 3/2012 | Konstantino et al. ........ 606/159 |

FOREIGN PATENT DOCUMENTS

| | | |
|---|---|---|
| WO | WO 2004/026357 | 4/2004 |
| WO | WO 2005/027996 | 3/2005 |
| WO | WO 2005/068533 A1 | 7/2005 |
| WO | WO 2006/101573 | 9/2006 |
| WO | WO 2009/111716 | 9/2009 |

OTHER PUBLICATIONS

International Search Report and Written Opinion dated Oct. 28, 2011.

* cited by examiner

CATHETER ASSEMBLY

CROSS REFERENCE TO RELATED APPLICATIONS

This application claims benefit of Provisional Application No. 61/360,354, filed Jun. 30, 2010, which application is incorporated herein by reference.

BACKGROUND

The release of drugs from an implanted medical device has been shown to be beneficial for the function of devices and the treatment of various medical conditions. For example, delivery of a drug from the device surface can prevent cellular responses initiated by the presence of the implantable device. Also, drug released from the device can prevent conditions that would otherwise shorten the functional life of the device following implantation. Drug released from the device may also be directed at treating a diseased area of the body.

Some implantable devices simply have a drug applied to the device surface. Such preparations are generally undesirable because the drug can be easily removed from the surface during insertion.

Implantable medical devices having thin polymeric coatings containing therapeutic compounds protect and control the release of drug from the device surface. Such devices have been shown to be particularly valuable for the treatment of diseases of the cardiovascular system. However, these polymeric coatings may not be ideal for applications involving the transient insertion of a medical device to a target tissue in the body.

SUMMARY

An aspect of the present disclosure relates to a catheter assembly. The catheter assembly includes an expandable and collapsible structure having an outer surface. The expandable and collapsible structure is adapted to expand between a contracted state and a dilated state. A coating is disposed on the outer surface of the expandable and collapsible structure. The coating includes a bioactive agent. A sleeve is disposed over the coating. The sleeve is adapted to expand between a compressed state and an enlarged state and to return to the compressed state. The sleeve defines a plurality of openings in the compressed state. An outer diameter of the coating is less than an outer diameter of the sleeve when the expandable and collapsible structure is in the contracted state and greater than the outer diameter of the sleeve when the expandable and collapsible structure is in the dilated state.

Another aspect of the present disclosure relates to a catheter assembly. The catheter assembly includes an expandable and collapsible structure having an outer surface. The expandable and collapsible structure is adapted to expand between a contracted state and a dilated state. A first coating is disposed on the outer surface of the expandable and collapsible structure. The first coating includes a bioactive agent. A second coating is disposed on the first coating. The second coating includes a mixture of fatty acids. A sleeve is disposed over the second coating. The sleeve is adapted to expand between a compressed state and an enlarged state. The sleeve includes a plurality of rails that extend longitudinally between a first axial end and an oppositely disposed second axial end. The plurality of rails defines a plurality of openings. The second coating is accessible through the openings in the compressed state. A size of each of the openings increases in the enlarged state.

Another aspect of the present disclosure relates to a catheter assembly. The catheter assembly includes an expandable and collapsible structure having an outer surface. The expandable and collapsible structure is adapted to expand between a contracted state and a dilated state. A first coating is disposed on the outer surface of the expandable and collapsible structure. The first coating includes a bioactive agent. A second coating is disposed on the first coating. The second coating includes a mixture of fatty acids. A sleeve is disposed over the second coating. The sleeve is adapted to expand between a compressed state and an enlarged state. The sleeve includes a body having an interior surface and an exterior surface. The interior surface defines a bore in which the expandable and collapsible structure is disposed. The body defines a plurality of openings that extend through the interior and exterior surfaces. The plurality of openings define an area at the exterior surface in the compressed state that is about 40% to about 95% of a total surface area of the exterior surface in the compressed state.

Another aspect of the present disclosure relates to a sleeve for a catheter assembly. The sleeve includes a body having a first axial end, an oppositely disposed second axial end, an exterior surface and an oppositely disposed interior surface. The body defines a bore that extends through the first and second axial ends and a plurality of openings that pass through the exterior and interior surfaces. The body is adapted to expand from a compressed state to an enlarged state in response to a force acting on the interior surface and to return to the compressed state when the force is removed. The plurality of opening define an area at the exterior surface in the compressed state that is about 40% to about 95% of a total surface area of the exterior surface in the compressed state.

Another aspect of the present disclosure relates to a catheter assembly includes an expandable and collapsible structure having an outer surface. The expandable and collapsible structure is adapted to expand between a contracted state and a dilated state. The expandable and collapsible structure includes a distal end and an oppositely disposed proximal end. A sleeve is disposed about the outer surface of the expandable and collapsible structure. The sleeve includes a body having a first axial end, an oppositely disposed second axial end, an exterior surface and an oppositely disposed interior surface. The body defines a bore in which at least a portion of the expandable and collapsible structure is disposed. The bore extends through the first and second axial ends. The body defines a plurality of openings that pass through the exterior and interior surfaces. The body is adapted to expand from a compressed state to an enlarged state when the expandable and collapsible structure is in the dilated state and to return to the compressed state from the enlarged state when the expandable structure is in the contracted state. The plurality of opening define an area at the exterior surface in the compressed state that is about 40% to about 95% of a total surface area of the exterior surface in the compressed state.

A variety of additional aspects will be set forth in the description that follows. These aspects can relate to individual features and to combinations of features. It is to be understood that both the foregoing general description and the following detailed description are exemplary and explanatory only and are not restrictive of the broad concepts upon which the embodiments disclosed herein are based.

DRAWINGS

DETAILED DESCRIPTION

Reference will now be made in detail to the exemplary aspects of the present disclosure that are illustrated in the accompanying drawings. Wherever possible, the same reference numbers will be used throughout the drawings to refer to the same or like structure.

Figure 1:
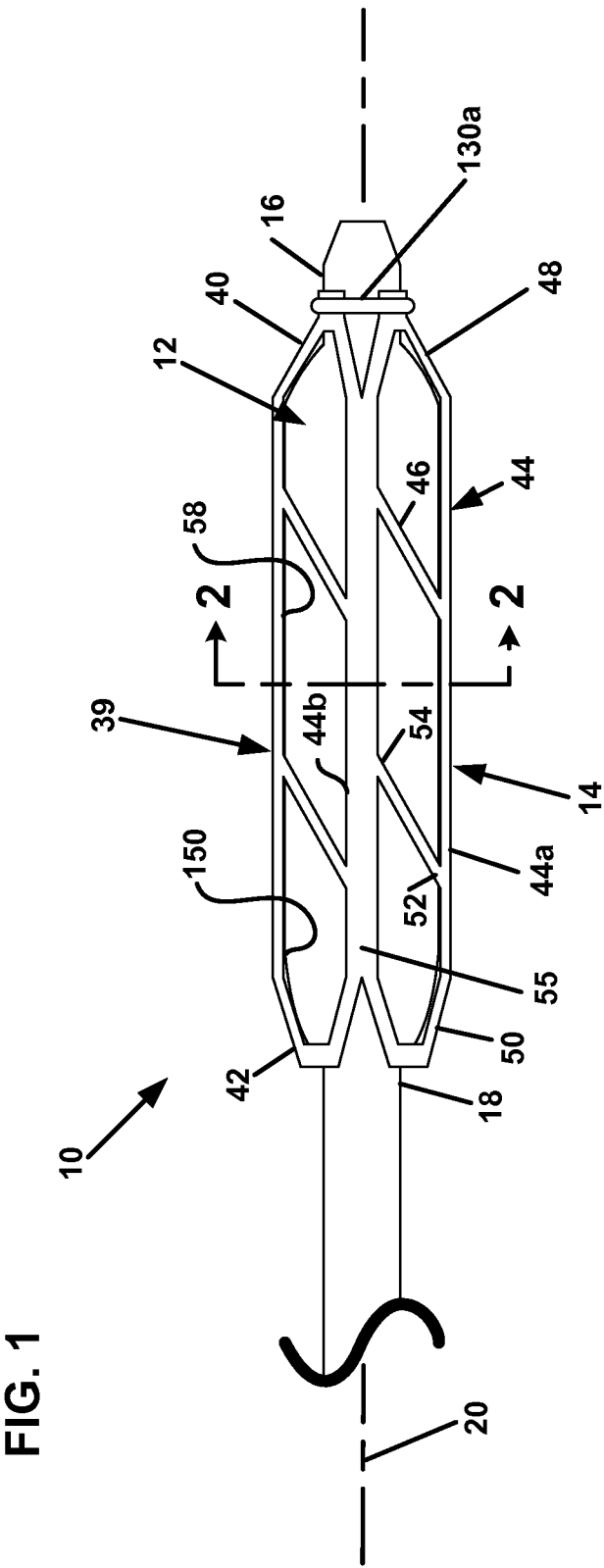
FIG. 1 is a side view of a catheter assembly, in which an expandable and collapsible structure is in a contracted state and a sleeve is in a compressed state, having exemplary features of aspects in accordance with the principles of the present disclosure.

Referring now to FIG. 1, a catheter assembly 10 is shown. The catheter assembly 10 is adapted to provide a drug delivery system that protects a drug layer as the catheter assembly 10 is guided to a target site.

In the depicted embodiment, the catheter assembly 10 is adapted for use in medical procedures such as angioplasty. In an angioplasty procedure, the catheter assembly 10 is inserted into a blood vessel of a patient and guided to a target site in the vasculature of the patient. In one example, the target site is a location at which there is a blockage in a blood vessel that is restricting flow through that blood vessel.

The catheter assembly 10 includes an expandable and collapsible structure 12 and a sleeve 14. The expandable and collapsible structure 12 of the catheter assembly 10 is expanded from a contracted state (shown in FIG. 1) to a dilated state (shown in FIG. 18) at the target site and subsequently collapsed from the dilated state to the contracted state. In one example, the dilation of the expandable and collapsible structure 12 compresses artheroma at the target site in the blood vessel. A coating disposed on the expandable and collapsible structure 12 is delivered to the tissue at or surrounding the target site when the expandable and collapsible structure 12 is in the dilated state. Referring now to the figures of the present disclosure, the catheter assembly 10 and the use of the catheter assembly 10 will be further described.

Figure 2:
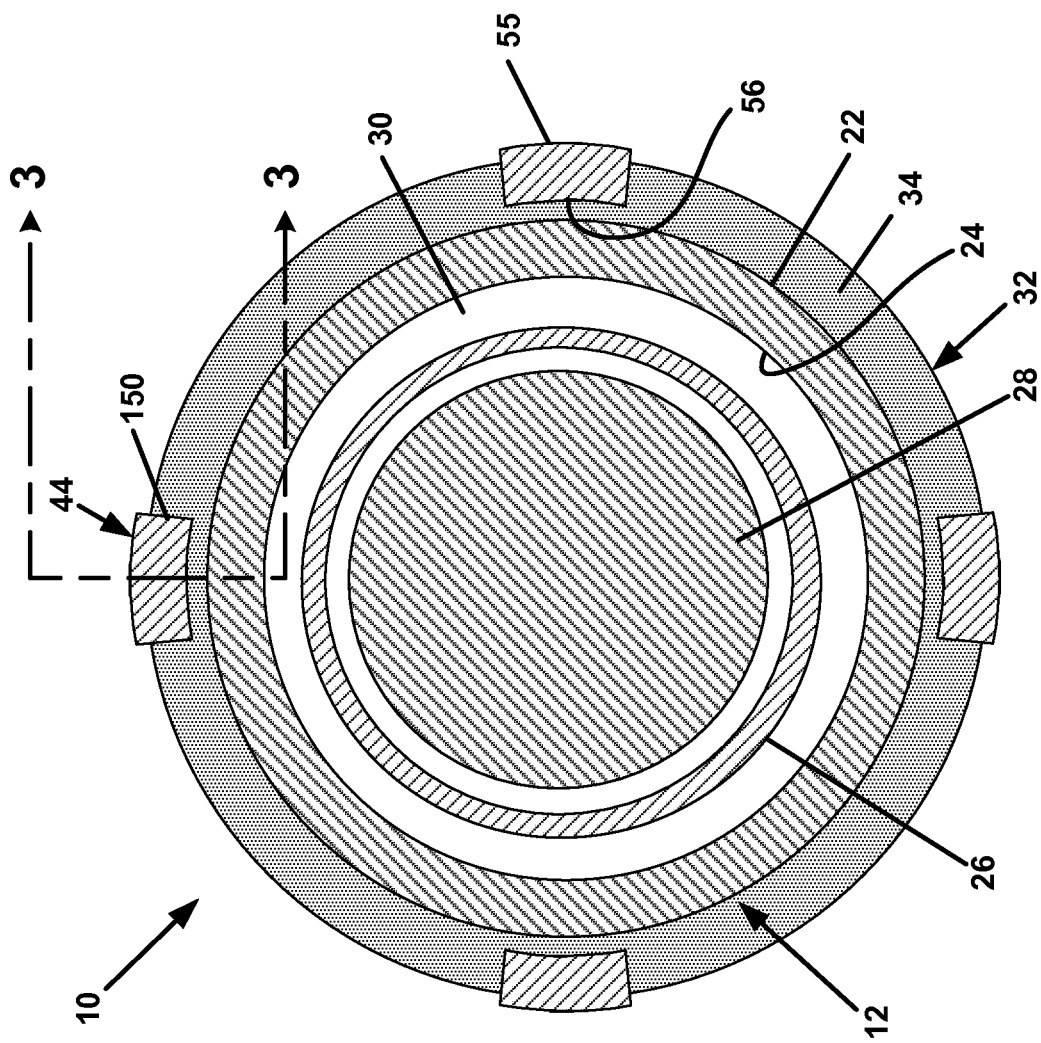
FIG. 2 is a cross-sectional view of the catheter assembly taken on line 2-2 of FIG. 1.

Referring now to FIGS. 1 and 2, the expandable and collapsible structure 12 includes distal end 16 and a proximal end 18 and defines a central longitudinal axis 20 that extends through the distal and proximal ends 16, 18. The expandable and collapsible structure 12 has an outer surface 22 that extends between the distal and proximal ends 16, 18 and an oppositely disposed inner surface 24. The expandable and collapsible structure 12 further includes a guide passage 26 that extends through the distal and proximal ends 16 and 18. The guide passage 26 is adapted to receive a guide wire 28 along which the catheter assembly 10 passes to the target site in the blood vessel of a body of the patient.

The expandable and collapsible structure 12 defines a lumen 30 disposed between the inner surface 24 of the expandable and collapsible structure 12 and the guide passage 26. The lumen 30 is adapted to receive a fluid (e.g., saline) to expand the expandable and collapsible structure 12 to the dilated state. When fluid is communicated to the lumen 30, the fluid exerts a radially outward force on the inner surface 24 of the expandable and collapsible structure 12. This radially outward force causes the expandable and collapsible structure 12 to dilate to the dilated state. When the fluid in the lumen 30 is drained, the expandable and collapsible structure 12 collapses or shrinks to the contracted state.

Figure 3:
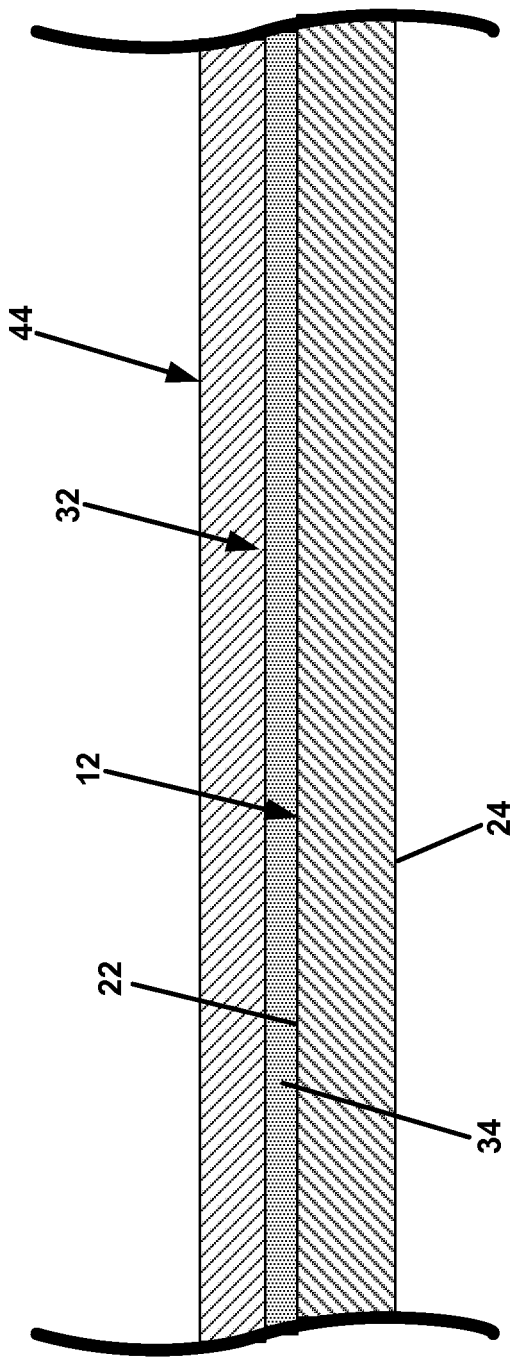
FIG. 3 is a cross-sectional view of the catheter assembly taken on line 3-3 of FIG. 2.

Referring now to FIGS. 2 and 3, the expandable and collapsible structure 12 includes a coating 32 disposed over the outer surface 22 of the expandable and collapsible structure 12. A coating suitable for use as the coating 32 of the catheter assembly 10 has been described in U.S. Patent Application Ser. No. 61/360,212, entitled "Lipid Coating for Medical Devices Delivering Bioactive Agent," filed on Jun. 30, 2010, the disclosure of which is hereby incorporated by reference in its entirety.

The coating 32 can include multiple coating layers. In the depicted embodiment of FIG. 2, the coating 32 includes an agent coating 34. The agent coating 34 is adapted to locally administer a bioactive agent to the target site in the body of the patient.

Coatings

The present medical device can include any of a variety of coatings including a bioactive agent. Numerous suitable coatings and polymers useful in such coatings are described herein. Certain embodiments suitable for release of bioactive agent from the expandable and collapsible structure can release effective amounts of the bioactive agent at the delivery site in seconds or minutes. The bioactive agent can be in an amorphous form incorporated into the coating or polymer matrix of the coating.

The coating including the bioactive agent can be on one or more portions of the expandable and collapsible structure, for example, on one or more portions of an exterior surface. The coating including the bioactive agent can cover the entire surface of the balloon portion of a balloon catheter. In that manner, when the balloon is expanded in situ, the bioactive agent can be transferred to the circumference of the lumen of the artery.

The coating including the bioactive agent can cover less than the entire surface of the expandable and collapsible structure, such as in a non-contiguous pattern. A "non-contiguous" coating refers to a coating material that does not cover the structure (e.g., the entire balloon surface), but rather formed at one or more portions of the surface. Non-contiguous coating patterns facilitate delamination of a biodegradable coated material from the expandable and collapsible surface when it is expanded. In some aspects, a non-contiguous biodegradable coating may experience little or no fracturing before it becomes delaminated from the surface. In other aspects, a non-contiguous biodegradable coatings can have a pattern that is easy to fracture, which facilitates delamination. In terms of inflation pressure, non-contiguous biodegradable coatings may require less force for coating delamination.

Biodegradable coatings having a non-contiguous pattern can be formed directly on the expandable and collapsible surface of a balloon, or can be formed in association with another coated material, such as a flexible hydrogel layer. Non-contiguous patterns, such as dotted and striped patterns, can be formed using a spray coating apparatus.

The coating including the bioactive agent can be a flexible hydrogel matrix. The flexible hydrogel matrix can be made from a biostable hydrophilic polymer. The polymer can be covalently bonded to the expandable and collapsible structure, covalently bonded to other hydrophilic polymers in the matrix, or both. In some desired aspects, the biostable hydrophilic polymer is bonded to the substrate surface via reacted photogroups.

The coating including the bioactive agent can include a water-soluble polymer, for example, a water-soluble polymer such as poly(vinylpyrolidone). In some cases, the coating includes a polymer that is covalently bonded to the surface of expandable and collapsible structure via reacted photogroups. The coating can also be formed from a composition in which the water-soluble polymer is in macromer form.

In an embodiment, at least a portion of the coating including the bioactive agent is capable of becoming delaminated upon expansion of the expandable and collapsible structure in the subject. The delaminated biodegradable polymeric matrix with bioactive agent can, for example, adhere to the target tissue. Degradation of the delaminated polymeric matrix and release of the bioactive agent can occur at the target site. The biodegradable polymeric matrix can be used in association with the flexible hydrogel matrix. The flexible hydrogel matrix can be the release coating. The biodegradable polymeric matrix can include the bioactive agent.

In an embodiment, the bioactive agent can be embedded in and/or attached to a fracturable, biodegradable coating that is present on the expandable and collapsible structure. In a non-expanded state, the bioactive material is substantially or entirely entrapped in the coating, or adhered to a coated layer, or both. Upon expansion of the substrate, the coating fractures and delaminates from the expandable and collapsible surface. Therefore, the coating can have properties of rigidity and brittleness. At the target site, portions of the coating are transferred to tissue along with the entrapped bioactive agent. In some cases the portions of the transferred coating can adhere to the tissue and provide a barrier or skin to improve its immobilization. Along with degradation of the biodegradable coating materials, bioactive agent can be released to provide a therapeutic effect.

The present medical device can also include any of a variety of coatings that aid in delivering a bioactive agent. Such coatings include a release coating and an adhesion coating. Numerous suitable coatings and polymers useful in such coatings are described in a herein.

In an embodiment, the present medical device includes an adhesion coating. The adhesion coating can be on the expandable and contractible structure and can promote adhesion of the agent coating to the subject's tissue at the delivery site. For example, the adhesion coating can be on the agent coating. For example, adhesion components can be in the agent coating. The adhesion coating can include a cationic moiety or an adhesion protein. The adhesion protein can be or can include collagen, heparin, laminin, or mixture thereof. In an embodiment, the adhesion coating can provide adhesive material for binding to a lesion, such as a lesion in a blood vessel. Components of the lesion to which adhesion can occur include cells, collagen, cholesterol, lipoproteins, or calcifications.

The device can include a degradable coated layer present between the coating including the bioactive agent and the surface of the expandable and collapsible structure. For example, the degradable layer can be present as a base coat on the surface of the expandable and collapsible structure.

Coating Polymers

The coating can be formed from polymeric material (one or more polymers) that allows immobilization of the bioactive agent in a non-expanded state. The polymeric material can include one or more homopolymers, copolymers, combinations or blends thereof useful for forming the matrix. In an aspect, the polymeric material is used to form an flexible hydrogel matrix as the coating.

In some modes of preparation, a coating composition is formed that includes one or more matrix-forming polymer and bioactive agent. Generally, the coating material is chosen and used in a composition suitable for forming a matrix with the bioactive agent. In one mode of practice, a hydrophilic polymer is used to prepare an aqueous composition that also includes the bioactive agent. The bioactive agent can be water insoluble, meaning that it does not readily dissolve in water.

In other cases, bioactive agent is not included in a coating composition having the one or more matrix-forming polymer. In such a coating process, the bioactive agent is used in a subsequent coating step where they become associated with the coated polymeric matrix.

Generally, a coating composition includes an amount and type of polymeric material that provides suitable physical properties (such as elasticity and bioactive agent retention). In some aspects the amount of polymeric material used to form the matrix in the composition is at a concentration in the range of about 5 mg/mL to about 50 mg/mL, about 10 mg/mL to about 40 mg/mL, or about 10 mg/mL to about 20 mg/mL. In exemplary modes of practice the polymeric material is present in the coating composition at about 15 mg/mL.

The polymeric material can also include pendent photoreactive or polymerizable groups that can be activated to form a crosslinked matrix of polymer. The amount of polymer in the composition can also be chosen based on the level of derivatization with these groups.

One class of hydrophilic polymers useful as polymeric materials for matrix formation is synthetic hydrophilic polymers. Synthetic hydrophilic polymers that are biostable (i.e., that show no appreciable degradation in vivo) can be prepared from any suitable monomer including acrylic monomers, vinyl monomers, ether monomers, or combinations of any one or more of these types of monomers. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, dimethylacrylamide (DMA), and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these.

Examples of polymers that can be formed from these monomers include poly(acrylamide), poly(methacrylamide), poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers and vinyl pyrrolidone/(meth)acrylamide copolymers. Mixtures of homopolymers and/or copolymers can be used.

Examples of some acrylamide-based polymers, such as poly(N,N-dimethylacrylamide-co-aminopropylmethacrylamide) and poly(acrylamide-co-N,N-dimethylaminopropylmethacrylamide) are described in example 2 of U.S. Patent Pub. No. 2006/0030669 filed Sep. 17, 2004 (Taton et al.), the disclosure of which is incorporated herein by reference.

In some embodiments, the hydrophilic polymer is a vinyl pyrrolidone polymer, or a vinyl pyrrolidone/(meth)acrylamide copolymer such as poly(vinylpyrrolidone-co-methacrylamide). If a PVP copolymer is used, it can be a copolymer of vinylpyrrolidone and a monomer selected from the group of acrylamide monomers. Exemplary acrylamide monomers include (meth)acrylamide and (meth)acrylamide derivatives, such as alkyl(meth)acrylamide, as exemplified by dimethylacrylamide, and aminoalkyl(meth)acrylamide, as exemplified by aminopropylmethacrylamide and dimethylaminopropylmethacrylamide. For example, poly(vinylpyrrolidone-co-N,N-dimethylaminopropylmethacrylamide) is described in example 2 of U.S. Patent Pub. No. 2006/0030669 (Taton et al.).

In one embodiment, the polymers and copolymers as described are derivatized with one or more photoactivatable group(s). Exemplary photoreactive groups that can be pendent from biostable hydrophilic polymer include aryl ketones, such as acetophenone, benzophenone, anthraquinone, anthrone, quinone, and anthrone-like heterocycles. This provides a hydrophilic polymer having a pendent activatable photogroup that can be applied to the expandable and collapsible structure, and then treated with actinic radiation sufficient to activate the photogroups and cause covalent bonding to a target, such as the material of the expandable and collapsible structure. Use of photo-hydrophilic polymers can be used to provide a durable coating of a flexible hydrogel matrix, with the hydrophilic polymeric materials covalently bonded to the material of the expandable and collapsible structure.

A hydrophilic polymer having pendent photoreactive groups can be used to prepare the flexible hydrogel coating. Methods of preparing hydrophilic polymers having photoreactive groups are known in the art. For example, methods for the preparation of photo-PVP are described in U.S. Pat. No. 5,414,075, the disclosure of which is incorporated herein by reference. Methods for the preparation of photo-polyacrylamide are described in U.S. Pat. No. 6,007,833, the disclosure of which is incorporated herein by reference.

In another embodiment, the polymers and copolymers as described are derivatized with one or more polymerizable group(s). Polymers with pendent polymerizable groups are commonly referred to macromers. The polymerizable group(s) can be present at the terminal portions (ends) of the polymeric strand or can be present along the length of the polymer. In one embodiment polymerizable groups are located randomly along the length of the polymer. Polymerizable groups can be activated form a crosslinked matrix in which the bioactive agent is immobilized.

Optionally, the coating can include a cross-linking agent. A crosslinking agent can promote the association of polymers in the coating, or the bonding of polymers to the coated surface. The choice of a particular crosslinking agent can depend on the ingredients of the coating composition.

Suitable crosslinking agents include two or more activatable groups, which can react with the polymers in the composition. Suitable activatable groups include photoreactive groups as described herein, like aryl ketones, such as acetophenone, benzophenone, anthraquinone, anthrone, quinone, and anthrone-like heterocycles.

The photoactivatable cross-linking agent can be ionic, and can have good solubility in an aqueous composition. Thus, in some embodiments, at least one ionic photoactivatable cross-linking agent is used to form the coating. The ionic cross-linking agent can include an acidic group or salt thereof, such as selected from sulfonic acids, carboxylic acids, phosphonic acids, salts thereof, and the like. Exemplary counter ions include alkali, alkaline earths metals, ammonium, protonated amines, and the like.

Exemplary ionic photoactivatable cross-linking agents include 4,5-bis(4-benzoylphenylmethyleneoxy) benzene-1, 3-disulfonic acid or salt; 2,5-bis(4-benzoylphenylmethyleneoxy)benzene-1,4-disulfonic acid or salt; 2,5-bis(4-benzoylmethyleneoxy)benzene-1-sulfonic acid or salt; N,N-bis [2-(4-benzoylbenzyloxy)ethyl]-2-aminoethanesulfonic acid or salt, and the like. See U.S. Pat. No. 6,278,018, the disclosure of which is incorporated herein by reference.

Natural polymers can also be used to form the matrix. Natural polymers include polysaccharides, for example, polydextrans, carboxymethylcellulose, and hydroxymethylcellulose; glycosaminoglycans, for example, hyaluronic acid; polypeptides, for example, soluble proteins such as collagen, albumin, and avidin; and combinations of these natural polymers. Combinations of natural and synthetic polymers can also be used.

In one mode of practice, the bioactive agent includes a first polymer that has a lower Tg than a second polymer. The second polymer, which is harder, can reduce the rate of release of the bioactive agent from the matrix. For example, the Tg of a suitable first polymer such as PLGA is about 45° C., and the Tg of a suitable second polymer such as PLLA is about 55° C. In some aspects the difference between the Tg of the first and second polymer is about 5° C. or greater. In more specific aspects the difference between the Tg of the first and second polymer is about 10° C. or greater. In some aspects, the first and second polymers have Tgs of about 35° C. or greater. In more specific aspects the first and second polymers have Tgs in the range of about 35° C. to about 65° C.

Selection of the first and second polymers can also be based on other properties of the polymers such as molecular weight, solubility, and rheology.

In certain embodiments, the polymer matrix includes an amphiphilic copolymer, a low molecular weight hydrophobic polymer, an organogel, a deformable hydrogel, a plurality thereof, or a mixture thereof. In an embodiment, the coating including a bioactive agent includes or is made of an amphiphilic copolymer. Suitable amphiphilic copolymers include a lactide/glycolide/caprolatone/polyethylene glycol copolymer. Such a copolymer can include blocks of polyethylene glycol. Although not limiting to the present disclosure, it is believed that an amphiphilic copolymer includes hydrophobic domains that enhance solubility of hydrophobic drugs and hydrophilic domains absorb water allowing the coating to swell upon exposure to blood.

In an embodiment, the coating including a bioactive agent includes or is made of a hydrophobic polymer of low average molecular weight. Suitable low molecular weight hydrophobic polymers include a polylactide/glycolide/caprolactone copolymer.

In an embodiment, the agent coating includes one or more solvents and the bioactive agent. In an embodiment, the agent coating includes an organogel. In an embodiment, the agent coating includes a deformable hydrogel.

In an embodiment, the agent coating includes a lipid. Although not limiting to the present disclosure it is believed that the lipid can enhance adhesion and penetration of drug into tissue. Drug can be emulsified into a lipid carrier.

In an embodiment, the drug is dissolved or dispersed in a deformable polymer layer, e.g., a hydrophobic polymer, an organogel, or a deformable hydrogel. In an embodiment, such a coating can flow or escape from the balloon surface and conform or adhere to the tissue upon expansion of the balloon.

Biodegradable Polymer

The biodegradable polymer can include one or more (e.g., 1, 2, 3 or 4) specific biodegradable polymers, for use in forming an implant in vivo. Suitable polymers will be biodegradable and will be substantially soluble in the biocompatible solvent system. Specifically, the biodegradable polymer can have a solubility of at least about 50 g/L in the biocompatible solvent system, at 25° C. and 1 atm. In one embodiment, the biodegradable polymer will not include a polymer that is substantially insoluble in the biocompatible solvent system. In an embodiment, the biodegradable polymer will not include a biodegradable polymer that is substantially insoluble in water or bodily fluids.

Suitable specific classes of polymers include, e.g., polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, polysaccharides, chitin, chitosan, and copolymers, block copolymers, multi-block co-polymers, multi-block co-polymers with polyethylene glycol (PEG), polyols, terpolymers and mixtures thereof.

In one embodiment, the biodegradable polymer is a thermoplastic polymer.

In one embodiment, the biodegradable polymer has a viscosity of at least about 100 cP at 37° C. In other embodiments, the biodegradable polymer has a viscosity of about 1,000 cP to about 30,000 cp at 37° C., about 5,000 cP to about 25,000 cp at 37° C., or about 10,000 cP to about 20,000 cp at 37° C.

In one embodiment, the biodegradable polymer is hydrophobic.

In one embodiment, the biodegradable polymer includes a block copolymer. In an embodiment, the biodegradable polymer is a polyethylene glycol (PEG) containing tri-block co-polymer.

In one embodiment the polymer contains functional side groups.

The biodegradable polymer can be present in any suitable and effective amount, provided the biodegradable polymer is substantially soluble in the solvent system, and in combination with the solvent system will form an implant in vivo. In one embodiment, the biodegradable polymer is present in about 10 wt. % to about 40 wt. % of the formulation. In an embodiment, the biodegradable polymer is present in about 40 wt. % to about 90 wt. % of the formulation.

In one embodiment, the biodegradable polymer can include a poly(ether ester) multi-block copolymer, for example, that sold under the trade name SynBiosys™. In an embodiment, the biodegradable polymer can include a polyglycerol fatty acid ester. In an embodiment, the biodegradable polymer can include a PEG-PBT polymer. In an embodiment, the biodegradable polymer can include a poly(ester-amide) polymer (PEA).

Poly(ether ester) Multi-Block Copolymers

One suitable class of biodegradable polymers includes the poly(ether ester) multi-block copolymers. These multi-block copolymers are composed of various pre-polymer building blocks of different combinations of DL-lactide, glycolide, ε-caprolactone and polyethylene glycol. By varying the molecular composition, molecular weight (Mw 1200-6000) and ratio of the pre-polymer blocks, different functionalities can be introduced into the final polymer, which enables the creation of polymers with various physio-chemical properties. Both hydrophobic as well as hydrophilic/swellable polymers and slowly degrading as well as rapidly degrading polymers can be designed.

The poly(ether ester) multi-block copolymers can include a polymer as shown below (formula III):

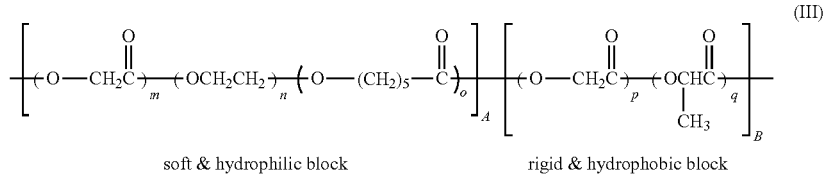

wherein,
m and p are each independently glycolide;
n is polyethylene glycol, Mw 300-1000;
o is ε-caprolactone; and
q is DL-lactide.

Under physiological conditions, such poly(ether ester) multi-block copolymers can degrade completely via hydrolysis into non-toxic degradation products which are metabolized and/or excreted through the urinary pathway. Consequently, there can be no accumulation of biomaterials, thereby reducing the chance of long-term foreign body reactions.

Additional features and descriptions of the poly(ether ester) multi-block copolymers are provided, for example, in Published PCT Patent Application No. WO 2005/068533 and references cited therein. An overview is provided below.

The multi-block copolymers can specifically include two hydrolysable segments having a different composition, linked by a multifunctional, specifically an aliphatic chain-extender, and which are specifically essentially completely amorphous under physiological conditions (moist environment, body temperature, which is approximately 37° C. for humans).

The resulting multi-block copolymers can specifically have a structure according to any of the formulae (1)-(3):

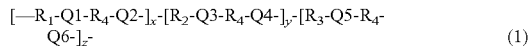

(1)

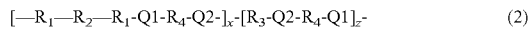

(2)

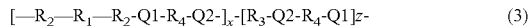

(3)

wherein:

$R_1$ and $R_2$ can be amorphous polyester, amorphous poly ether ester or amorphous polycarbonate; or an amorphous pre-polymer that is obtained from combined ester, ether and/or carbonate groups. $R_1$ and $R_2$ can contain polyether groups, which can result from the use of these compounds as a polymerization initiator, the polyether being amorphous or crystalline at room temperature. However, the polyether thus introduced will become amorphous at physiological conditions. $R_1$ and $R_2$ are derived from amorphous pre-polymers or blocks A and B, respectively, and $R_1$ and $R_2$ are not the same. $R_1$ and $R_2$ can contain a polyether group at the same time. In a specific embodiment, only one of them will contain a polyether group;

z is zero or a positive integer;

$R_3$ is a polyether, such as poly(ethylene glycol), and may be present (z≠0) or not (z=0). $R_3$ will become amorphous under physiological conditions;

$R_4$ is an aliphatic $C_2$-$C_8$ alkylene group, optionally substituted by a $C_1$-$C_{10}$ alkylene, the aliphatic group being linear or cyclic, wherein $R_4$ can specifically be a butylene, —$(CH_2)_4$— group, and the $C_1$-$C_{10}$ alkylene side group can contain protected S, N, P or O moieties;

x and y are both positive integers, which can both specifically be at least 1, whereas the sum of x and y (x+y) can specifically be at most 1000, more specifically at most 500, or at most 100. Q1-Q6 are linking units obtained by the reaction of the pre-polymers with the multifunctional chain-extender. Q1-Q6 are independently amine, urethane, amide, carbonate, ester or anhydride. The event that all linking groups Q are different being rare and not preferred.

Typically, one type of chain-extender can be used with three pre-polymers having the same end-groups, resulting in a copolymer of formula (1) with six similar linking groups. In case pre-polymers $R_1$ and $R_2$ are differently terminated, two types of groups Q will be present: e.g. Q1 and Q2 will be the same between two linked pre-polymer segments $R_1$, but Q1 and Q2 are different when $R_1$ and $R_2$ are linked. Obviously, when Q1 and Q2 are the same, it means that they are the same type of group but as mirror images of each other.

In copolymers of formula (2) and (3) the groups Q1 and Q2 are the same when two pre-polymers are present that are both terminated with the same end-group (which is usually hydroxyl) but are different when the pre-polymers are differently terminated (e.g. PEG which is diol terminated and a di-acid terminated 'tri-block' pre-polymer). In case of the tri-block pre-polymers ($R_1R_2R_1$ and $R_2R_1R_2$), the outer segments should be essentially free of PEG, because the coupling reaction by ring opening can otherwise not be carried out successfully. Only the inner block can be initiated by a PEG molecule.

The examples of formula (1), (2) and (3) show the result of the reaction with a di-functional chain-extender and di-functional pre-polymers.

With reference to formula (1) the polyesters can also be represented as multi-block or segmented copolymers having a structure (ab)n with alternating a and b segments or a structure (ab)r with a random distribution of segments a and b, wherein 'a' corresponds to the segment $R_1$ derived from pre-polymer (A) and 'b' corresponds to the segment $R_2$ derived from pre-polymer (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the pre-polymers. Specifically, this is a di-functional chain-extender. In case z≠0, then the presentation of a random distribution of all the segments can be given by (abc)r were three different pre-polymers (one being e.g. a polyethylene glycol) are randomly distributed in all possible ratio's. The alternating distribution is given by (abc)n. In this particular case, alternating means that two equally terminated pre-polymers (either a and c or b and c) are alternated with a differently terminated pre-polymer b or a, respectively, in an equivalent amount (a+c=b or b+c=a). Those according to formula (2) or (3) have a structure (aba)n and (bab)n wherein the aba and bab 'triblock' pre-polymers are chain-extended with a di-functional molecule.

The method to obtain a copolymer with a random distribution of a and b (and optionally c) is far more advantageous than when the segments are alternating in the copolymer such as in (ab)n with the ratio of pre-polymers a and b being 1. The composition of the copolymer can then only be determined by adjusting the pre-polymer lengths. In general, the a and b segment lengths in (ab)n alternating copolymers are smaller than blocks in block-copolymers with structures ABA or AB.

The pre-polymers of which the a and b (and optionally c) segments are formed in (ab)r, (abc)r, (ab)n and (abc)n are linked by the di-functional chain-extender. This chain-extender can specifically be a diisocyanate chain-extender, but can also be a diacid or diol compound. In case all pre-polymers contain hydroxyl end-groups, the linking units will be urethane groups. In case (one of) the pre-polymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodiimide) forming ester linkages. In (aba)n and (bab)n the aba and bab pre-polymers are also specifically linked by an aliphatic di-functional chain-extender, more specifically, a diisocyanate chain-extender.

The term "randomly segmented" copolymers refers to copolymers that have a random distribution (i.e. not alternating) of the segments a and b: (ab)r or a, b and c: (abc)r.

PEG-PBT polymers

One suitable class of biodegradable polymers includes the poly(ether ester) multiblock copolymers based on poly(ethylene glycol) (PEG) and poly(butylene terephthalate) (PBT), that can be described by the following general formula IV:

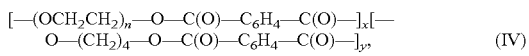

$$[-(OCH_2CH_2)_n-O-C(O)-C_6H_4-C(O)-]_x[-O-(CH_2)_4-O-C(O)-C_6H_4-C(O)-]_y, \quad (IV)$$

wherein,

—$C_6H_4$— designates the divalent aromatic ring residue from each esterified molecule of terephthalic acid, n represents the number of ethylene oxide units in each hydrophilic PEG block, x represents the number of hydrophilic blocks in the copolymer, and y represents the number of hydrophobic blocks in the copolymer.

In specific embodiments, n can be selected such that the molecular weight of the PEG block is between about 300 and about 4000. In specific embodiments, x and y can each be independently selected so that the multiblock copolymer contains from about 55% up to about 80% PEG by weight.

The block copolymer can be engineered to provide a wide array of physical characteristics (e.g., hydrophilicity, adherence, strength, malleability, degradability, durability, flexibility) and bioactive agent release characteristics (e.g., through controlled polymer degradation and swelling) by varying the values of n, x and y in the copolymer structure.

Polyester Amides

One suitable class of biodegradable polymers includes the polyesteramide polymers having a subunit of the formula (V):

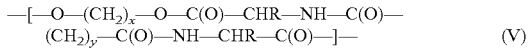

$$-[-O-(CH_2)_x-O-C(O)-CHR-NH-C(O)-(CH_2)_y-C(O)-NH-CHR-C(O)-]- \quad (V)$$

wherein, x is $C_2$-$C_{12}$, y is $C_2$-$C_{12}$, and

R is —$CH(CH_3)_2$, —$CH_2CH(CH_3)_2$, —$CH(CH_3)$ $CH_2CH_3$, —$CH_2(CH_2)_2CH_3$, —$CH_2C_6H_5$, —$CH_2(CH_2)_2SCH_3$ or part of an amino acid.

In specific embodiments, the $C_2$-$C_{12}$ can be ($C_2$-$C_{12}$) alkyl. In other specific embodiments, the $C_2$-$C_{12}$ can be ($C_2$-$C_{12}$) alkyl, optionally substituted.

Such polymers are described, for example, in U.S. Pat. No. 6,703,040. Polymers of this nature can be described with a nomenclature of x-aa-y, wherein "x" represents an alkyl diol with x carbon atoms, "aa" represents an amino acid such as leucine or phenylalanine, and y represents an alkyldicarboxylic acid with y carbon atoms, and wherein the polymer is a polymerization of the diol, the dicarboxylic acid, and the amino acid. An exemplary polymer of this type is 4-Leu-4.

Poly(ester-amide) Polymer (PEA)

One suitable class of biodegradable polymers includes the poly(ester-amide) polymers. Such polymers can be prepared by polymerization of a diol, a dicarboxylic acid and an alpha-amino acid through ester and amide links in the form $(DACA)_n$. An example of a $(DACA)_n$ polymer is shown below in formula VI. Suitable amino acids include any natural or synthetic alpha-amino acid, specifically neutral amino acids.

Diols can be any aliphatic diol, including alkylene diols like HO—$(CH_2)_k$—OH (i.e. non-branched), branched diols (e.g., propylene glycol), cyclic diols (e.g. dianhydrohexitols and cyclohexanediol), or oligomeric diols based on ethylene glycol (e.g., diethylene glycol, triethylene glycol, tetraethylene glycol, or poly(ethylene glycol)s). Aromatic diols (e.g., bis-phenols) are less useful for these purposes since they are more toxic, and polymers based on them have rigid chains that are less likely to biodegrade.

Dicarboxylic acids can be any aliphatic dicarboxylic acid, such as comega-dicarboxylic acids (i.e., non-branched), branched dicarboxylic acids, cyclic dicarboxylic acids (e.g. cyclohexanedicarboxylic acid). Aromatic diacids (like phthalic acids, etc.) are less useful for these purposes since they are more toxic, and polymers based on them have rigid chain structure, exhibit poorer film-forming properties and have much lower tendency to biodegrade.

Specific PEA polymers have the formula VI:

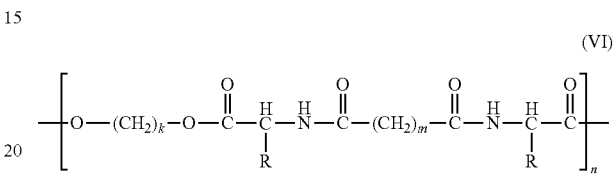

(VI)

wherein, k is 2-12 (e.g., 2, 3, 4, or 6);

m is 2-12 (e.g., 4 or 8); and

R is —$CH(CH_3)_2$, —$CH_2CH(CH_3)_2$, —$CH(CH_3)$ $CH_2CH_3$, —$CH_2(CH_2)_2CH_3$, —$CH_2(C_6H_5)$, or —$CH_2(CH_2)SCH_3$.

In specific embodiments, A is L-phenylalanine (Phe-PEA) and A is L-leucine (Leu-PEA). In specific embodiments, the ratio of Phe-PEA to Leu-PEA is from 10:1 to 1:1. In other specific embodiments, the ratio of Phe-PEA to Leu-PEA is from 5:1 to 2.5:1.

Additional features and descriptions of the poly(esteramide) polymers (PEA) are provided, for example, in U.S. Pat. No. Re 40,359, which is a reissue of U.S. Pat. No. 6,703,040.

Hydrophobic Derivatives of Natural Biodegradable Polysaccharides

One suitable class of biodegradable polymers includes the hydrophobic derivatives of natural biodegradable polysaccharides, such as those sold under the trade name Eureka™ SOLO polymers. Hydrophobic derivatives of natural biodegradable polysaccharide refer to a natural biodegradable polysaccharide having one or more hydrophobic pendent groups attached to the polysaccharide. In many cases the hydrophobic derivative includes a plurality of groups that include hydrocarbon segments attached to the polysaccharide. When a plurality of groups including hydrocarbon segments are attached, they are collectively referred to as the "hydrophobic portion" of the hydrophobic derivative. The hydrophobic derivatives therefore include a hydrophobic portion and a polysaccharide portion.

The polysaccharide portion includes a natural biodegradable polysaccharide, which refers to a non-synthetic polysaccharide that is capable of being enzymatically degraded. Natural biodegradable polysaccharides include polysaccharide and/or polysaccharide derivatives that are obtained from natural sources, such as plants or animals. Natural biodegradable polysaccharides include any polysaccharide that has been processed or modified from a natural biodegradable polysaccharide (for example, maltodextrin is a natural biodegradable polysaccharide that is processed from starch). Exemplary natural biodegradable polysaccharides include maltodextrin, amylose, cyclodextrin, polyalditol, hyaluronic acid, dextran, heparin, chondroitin sulfate, dermatan sulfate, heparan sulfate, keratan sulfate, dextran, dextran sulfate, pentosan polysulfate, and chitosan. Specific polysaccharides are low molecular weight polymers that have little or no branching, such as those that are derived from and/or found in starch preparations, for example, maltodextrin, amylose, and cyclodextrin. Therefore, the natural biodegradable polysaccharide can be a substantially non-branched or completely non-branched poly(glucopyranose) polymer.

"Amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1\times10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1\times10^7$ Da or greater.

For example, in some aspects, starch preparations having a high amylose content, purified amylose, synthetically prepared amylose, or enriched amylose preparations can be used in the preparation of a hydrophobic derivative of amylose. In starch sources, amylose is typically present along with amylopectin, which is a branched polysaccharide. If a mixture of amylose and a higher molecular weight precursor is used (such as amylopectin), amylose can be present in the composition in an amount greater than the higher molecular weight precursor. For example, in some aspects, starch preparations having high amylose content, purified amylose, synthetically prepared amylose, or enriched amylose preparations can be used in the preparation of a hydrophobic derivative of amylose polymer. In some embodiments the composition includes a mixture of polysaccharides including amylose wherein the amylose content in the mixture of polysaccharides is 50% or greater, 60% or greater, 70% or greater, 80% or greater, or 85% or greater by weight. In other embodiments the composition includes a mixture of polysaccharides including amylose and amylopectin and wherein the amylopectin content in the mixture of polysaccharides is 30% or less, or 15% or less.

The amount of amylopectin present in a starch may also be reduced by treating the starch with amylopectinase, which cleaves α-1,6 linkages resulting in the debranching of amylopectin into amylose.

Steps may be performed before, during, and/or after the process of derivatizing the amylose polymer with a pendent group comprising a hydrocarbon segment to enrich the amount of amylose, or purify the amylose.

Amylose of particular molecular weights can be obtained commercially or can be prepared. For example, synthetic amyloses with average molecular masses of 70 kDa, 110 kDa, and 320 kDa, can be obtained from Nakano Vinegar Co., Ltd. (Aichi, Japan). The decision of using amylose of a particular size range may depend on factors such as the physical characteristics of the composition (e.g., viscosity), the desired rate of degradation of the implant, and the nature and amount of the active pharmaceutical ingredient (API).

Purified or enriched amylose preparations can be obtained commercially or can be prepared using standard biochemical techniques such as chromatography. In some aspects, high-amylose cornstarch can be used to prepare the hydrophobic derivative.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate×100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500 Da to 5000 Da are commercially available (for example, from CarboMer, San Diego, Calif.).

Another contemplated class of natural biodegradable polysaccharides is natural biodegradable non-reducing polysaccharides. A non-reducing polysaccharide can provide an inert matrix thereby improving the stability of active pharmaceutical ingredients (APIs), such as proteins and enzymes. A non-reducing polysaccharide refers to a polymer of non-reducing disaccharides (two monosaccharides linked through their anomeric centers) such as trehalose (α-D-glucopyranosyl α-D-glucopyranoside) and sucrose (β-D-fructofuranosyl α-D-glucopyranoside). An exemplary non-reducing polysaccharide includes polyalditol which is available from GPC (Muscatine, Iowa). In another aspect, the polysaccharide is a glucopyranosyl polymer, such as a polymer that includes repeating (1→3)O-β-D-glucopyranosyl units.

Dextran is an α-D-1,6-glucose-linked glucan with side-chains 1-3 linked to the backbone units of the dextran biopolymer. Dextran includes hydroxyl groups at the 2, 3, and 4 positions on the glucopyranose monomeric units. Dextran can be obtained from fermentation of sucrose-containing media by *Leuconostoc mesenteroides* B512F.

Dextran can be obtained in low molecular weight preparations. Enzymes (dextranases) from molds such as *Penicillium* and *Verticillium* have been shown to degrade dextran. Similarly many bacteria produce extracellular dextranases that split dextran into low molecular weight sugars.

Chondroitin sulfate includes the repeating disaccharide units of D-galactosamine and D-glucuronic acid, and typically contains between 15 to 150 of these repeating units. Chondroitinase AC cleaves chondroitin sulfates A and C, and chondroitin.

Hyaluronic acid (HA) is a naturally derived linear polymer that includes alternating β-1,4-glucuronic acid and β-1,3-N-acetyl-D-glucosamine units. HA is the principal glycosaminoglycan in connective tissue fluids. HA can be fragmented in the presence of hyaluronidase.

In many aspects the polysaccharide portion and the hydrophobic portion include the predominant portion of the hydrophobic derivative of the natural biodegradable polysaccharide. Based on a weight percentage, the polysaccharide portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. Likewise, based on a weight percentage of the overall hydrophobic derivative, the hydrophobic portion can be about 25% wt of the hydrophobic derivative or greater, in the range of about 25% to about 75%, in the range of about 30% to about 70%, in the range of about 35% to about 65%, in the range of about 40% to about 60%, or in the range of about 45% to about 55%. In exemplary aspects, the hydrophobic derivative has approximately 50% of its weight attributable to the polysaccharide portion, and approximately 50% of its weight attributable to its hydrophobic portion.

The hydrophobic derivative has the properties of being insoluble in water. The term for insolubility is a standard term used in the art, and meaning 1 part solute per 10,000 parts or greater solvent. (see, for example, Remington: The Science and Practice of Pharmacy, 20th ed. (2000), Lippincott Williams & Wilkins, Baltimore Md.).

A hydrophobic derivative can be prepared by associating one or more hydrophobic compound(s) with a natural biodegradable polysaccharide polymer. Methods for preparing hydrophobic derivatives of natural biodegradable polysaccharides are described herein.

The hydrophobic derivatives of the natural biodegradable polysaccharides specifically have an average molecular weight of up to about 1,000,000 Da, up to about 300,000 Da or up to about 100,000 Da. Use of these molecular weight derivatives can provide implants with desirable physical and drug-releasing properties. In some aspects the hydrophobic derivatives have a molecular weight of about 250,000 Da or less, about 100,000 Da or less, about 50,000 Da or less, or 25,000 Da or less. Particularly specific size ranges for the natural biodegradable polysaccharides are in the range of about 2,000 Da to about 20,000 Da, or about 4,000 Da to about 10,000 Da.

The molecular weight of the polymer is more precisely defined as "weight average molecular weight" or $M_w$. $M_w$ is an absolute method of measuring molecular weight and is particularly useful for measuring the molecular weight of a polymer (preparation). Polymer preparations typically include polymers that individually have minor variations in molecular weight. Polymers are molecules that have a relatively high molecular weight and such minor variations within the polymer preparation do not affect the overall properties of the polymer preparation. The $M_w$ can be measured using common techniques, such as light scattering or ultracentrifugation. Discussion of $K_w$ and other terms used to define the molecular weight of polymer preparations can be found in, for example, Allcock, H. R. and Lampe, F. W. (1990) *Contemporary Polymer Chemistry*; pg 271.

The addition of hydrophobic portion will generally cause an increase in molecular weight of the polysaccharide from its underivatized, starting molecular weight. The amount increase in molecular weight can depend on one or more factors, including the type of polysaccharide derivatized, the level of derivation, and, for example, the type or types of groups attached to the polysaccharide to provide the hydrophobic portion.

In some aspects, the addition of hydrophobic portion causes an increase in molecular weight of the polysaccharide of about 20% or greater, about 50% or greater, about 75% or greater, about 100% or greater, or about 125%, the increase in relation to the underivatized form of the polysaccharide.

As an example, a maltodextrin having a starting weight of about 3000 Da is derivatized to provide pendent hexanoate groups that are coupled to the polysaccharide via ester linkages to provide a degree of substitution (DS) of about 2.5. This provides a hydrophobic polysaccharide having a theoretical molecular weight of about 8400 Da.

In forming the hydrophobic derivative of the natural biodegradable polysaccharide and as an example, a compound having a hydrocarbon segment can be covalently coupled to one or more portions of the polysaccharide. For example, the compound can be coupled to monomeric units along the length of the polysaccharide. This provides a polysaccharide derivative with one or more pendent groups. Each chemical group includes a hydrocarbon segment. The hydrocarbon segment can constitute all of the pendent chemical group, or the hydrocarbon segment can constitute a portion of the pendent chemical group. For example, a portion of the hydrophobic polysaccharide can have the following structural formula (1):

(I)

wherein each M is independently a monosaccharide unit, each L is independently a suitable linking group, or is a direct bond, each PG is independently a pendent group, each x is independently 0 to about 3, such that when x is 0, the bond between L and M is absent, and y is 3 or more.

Additionally, the polysaccharide that includes the unit of formula (1) above can be a compound of formula (II):

(II)

wherein each M is independently a monosaccharide unit, each L is independently a suitable linking group, or is a direct bond, each PG is independently a pendent group, each x is independently 0 to about 3, such that when x is 0, the bond between L and M is absent, y is about 3 to about 5,000, and $Z^1$ and $Z^2$ are each independently hydrogen, $OR^1$, $OC(=O)R^1$, $CH_2OR^1$, $SiR^1$ or $CH_2OC(=O)R^1$. Each $R^1$ is independently hydrogen, alkyl, cycloalkyl, cycloalkyl alkyl, aryl, aryl alkyl, heterocyclyl or heteroaryl, each alkyl, cycloalkyl, aryl, heterocycle and heteroaryl is optionally substituted, and each alkyl, cycloalkyl and heterocycle is optionally partially unsaturated.

For the compounds of formula (I) and (II), the monosaccharide unit (M) can include D-glucopyranose (e.g., α-D-glucopyranose). Additionally, the monosaccharide unit (M) can include non-macrocyclic poly-α(1→4) glucopyranose, non-macrocyclic poly-α(1→6) glucopyranose, or a mixture or combination of both non-macrocyclic poly-α(1→4) glucopyranose and non-macrocyclic poly-α(1→6) glucopyranose. For example, the monosaccharide unit (M) can include glucopyranose units, wherein at least about 90% are linked by α(1→4) glycosidic bonds. Alternatively, the monosaccharide unit (M) can include glucopyranose units, wherein at least about 90% are linked by α(1→6) glycosidic bonds. Additionally, each of the monosaccharides in the polysaccharide can be the same type (homopolysaccharide), or the monosaccharides in the polysaccharide can differ (heteropolysaccharide).

The polysaccharide can include up to about 5,000 monosaccharide units (i.e., y in the formula (1) or (II) is up to 5,000). Specifically, the monosaccharide units can be glucopyranose units (e.g., α-D-glucopyranose units). Additionally, y in the formula (1) or (II) can specifically be about 3-5,000 or about 3-4,000 or about 100 to 4,000.

In specific embodiments, the polysaccharide is non-macrocyclic. In other specific embodiments, the polysaccharide is linear. In other specific embodiments, the polysaccharide is branched. In yet further specific embodiments, the polysaccharide is a natural polysaccharide (PS).

The polysaccharide will have a suitable glass transition temperature (Tg). In one embodiment, the polysaccharide will have a glass transition temperature (Tg) of at least about 35° C. (e.g., about 40° C. to about 150° C.). In an embodiment, the polysaccharide will have a glass transition temperature (Tg) of +30° C. to about 0° C.

A "pendant group" refers to a group of covalently bonded carbon atoms having the formula $(CH_n)_m$, wherein m is 2 or greater, and n is independently 2 or 1. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. Specifically, the pendant group includes linear, straight chain or branched $C_1$-$C_{20}$ alkyl group; an amine terminated hydrocarbon or a hydroxyl terminated hydrocarbon. In an embodiment, the pendant group includes polyesters such as polylactides, polyglycolides, poly(lactide-co-glycolide) co-polymers, polycaprolactone, terpolymers of poly(lactide-co-glycolide-co-caprolatone), or combinations thereof.

The monomeric units of the hydrophobic polysaccharides described herein typically include monomeric units having ring structures with one or more reactive groups. These reactive groups are exemplified by hydroxyl groups, such as the ones that are present on glucopyranose-based monomeric units, e.g., of amylose and maltodextrin. These hydroxyl groups can be reacted with a compound that includes a hydrocarbon segment and a group that is reactive with the hydroxyl group (a hydroxyl-reactive group).

Examples of hydroxyl reactive groups include acetal, carboxyl, anhydride, acid halide, and the like. These groups can be used to form a hydrolytically cleavable covalent bond between the hydrocarbon segment and the polysaccharide backbone. For example, the method can provide a pendent group having a hydrocarbon segment, the pendent group linked to the polysaccharide backbone with a cleavable ester bond. In these aspects, the synthesized hydrophobic derivative of the natural biodegradable polysaccharide can include chemical linkages that are both enzymatically cleavable (the polymer backbone) and non-enzymatically hydrolytically cleavable (the linkage between the pendent group and the polymer backbone).

Other cleavable chemical linkages (e.g., metabolically cleavable covalent bonds) that can be used to bond the pendent groups to the polysaccharide include carboxylic ester, carbonate, borate, silyl ether, peroxyester groups, disulfide groups, and hydrazone groups.

In some cases, the hydroxyl reactive groups include those such as isocyanate and epoxy. These groups can be used to form a non-cleavable covalent bond between the pendent group and the polysaccharide backbone. In these aspects, the synthesized hydrophobic derivative of the natural biodegradable polysaccharide includes chemical linkages that are enzymatically cleavable.

Other reactive groups, such as carboxyl groups, acetyl groups, or sulphate groups, are present on the ring structure of monomeric units of other natural biodegradable polysaccharides, such as chondrotin or hyaluronic acid. These groups can also be targeted for reaction with a compound having a hydrocarbon segment to be bonded to the polysaccharide backbone.

Various factors can be taken into consideration in the synthesis of the hydrophobic derivative of the natural biodegradable polysaccharide. These factors include the physical and chemical properties of the natural biodegradable polysaccharide, including its size, and the number and presence of reactive groups on the polysaccharide and solubility, the physical and chemical properties of the compound that includes the hydrocarbon segment, including its the size and solubility, and the reactivity of the compound with the polysaccharide.

In preparing the hydrophobic derivative of the natural biodegradable polysaccharide any suitable synthesis procedure can be performed. Synthesis can be carried out to provide a desired number of groups with hydrocarbon segments pendent from the polysaccharide backbone. The number and/or density of the pendent groups can be controlled, for example, by controlling the relative concentration of the compound that includes the hydrocarbon segment to the available reactive groups (e.g., hydroxyl groups) on the polysaccharide.

The type and amount of groups having the hydrocarbon segment pendent from the polysaccharide is sufficient for the hydrophobic polysaccharide to be insoluble in water. In order to achieve this, as a general approach, a hydrophobic polysaccharide is obtained or prepared wherein the groups having the hydrocarbon segment pendent from the polysaccharide backbone in an amount in the range of 0.25 (pendent group): 1 (polysaccharide monomer) by weight.

The weight ratio of glucopyranose units to pendent groups can vary, but will typically be about 1:1 to about 100:1. Specifically, the weight ratio of glucopyranose units to pendent groups can be about 1:1 to about 75:1, or about 1:1 to about 50:1. Additionally, the nature and amount of the pendent group can provide a suitable degree of substitution to the polysaccharide. Typically, the degree of substitution will be in the range of about 0.1-5 or about 0.5-2.

To exemplify these levels of derivation, very low molecular weight (less than 10,000 Da) glucopyranose polymers are reacted with compounds having the hydrocarbon segment to provide low molecular weight hydrophobic glucopyranose polymers. In one mode of practice, the natural biodegradable polysaccharide maltodextrin in an amount of 10 g (MW 3000-5000 Da; ~3 mmols) is dissolved in a suitable solvent, such as tetrahydrofuran. Next, a solution having butyric anhydride in an amount of 18 g (0.11 mols) is added to the maltodextrin solution. The reaction is allowed to proceed, effectively forming pendent butyrate groups on the pyranose rings of the maltodextrin polymer. This level of derivation results in a degree of substitution (DS) of butyrate group of the hydroxyl groups on the maltodextrin of about 1.

For maltodextrin and other polysaccharides that include three hydroxyl groups per monomeric unit, on average, one of the three hydroxyl groups per glycopyranose monomeric unit becomes substituted with a butyrate group. A maltodextrin polymer having this level of substitution is referred to herein as maltodextrin-butyrate DS1. As described herein, the DS refers to the average number of reactive groups (including hydroxyl and other reactive groups) per monomeric unit that are substituted with pendent groups comprising hydrocarbon segments.

An increase in the DS can be achieved by incrementally increasing the amount of compound that provides the hydrocarbon segment to the polysaccharide. As another example, butyrylated maltodextrin having a DS of 2.5 is prepared by reacting 10 g of maltodextrin (MW 3000-5000 Da; ~3 mmols) with 0.32 mols butyric anhydride.

The degree of substitution can influence the hydrophobic character of the polysaccharide. In turn, implants formed from hydrophobic derivatives having a substantial amount of groups having the hydrocarbon segments bonded to the polysaccharide backbone (as exemplified by a high DS) are generally more hydrophobic and can be more resistant to degradation. For example, an implant formed from maltodextrin-butyrate DS1 has a rate of degradation that is faster than an implant formed from maltodextrin-butyrate DS2.

The type of hydrocarbon segment present in the groups pendent from the polysaccharide backbone can also influence the hydrophobic properties of the polymer. In one aspect, the implant is formed using a hydrophobic polysaccharide having pendent groups with hydrocarbon segments being short chain branched alkyl group. Exemplary short chain branched alkyl group are branched $C_4$-$C_{10}$ groups. The preparation of a hydrophobic polymer with these types of pendent groups is exemplified by the reaction of maltodextrin with valproic acid/anhydride with maltodextrin (MD-val). The reaction can be carried out to provide a relatively lower degree of substitution of the hydroxyl groups, such as is in the range of 0.5-1.5. Although these polysaccharides have a lower degree of substitution, the short chain branched alkyl group imparts considerable hydrophobic properties to the polysaccharide.

Even at these low degrees of substitution the MD-val forms coatings that are very compliant and durable. Because of the low degrees of substitution, the pendent groups with the branched $C_8$ segment can be hydrolyzed from the polysaccharide backbone at a relatively fast rate, thereby providing a biodegradable coatings that have a relatively fast rate of degradation.

For polysaccharides having hydrolytically cleavable pendent groups that include hydrocarbon segments, penetration by an aqueous solution can promote hydrolysis and loss of groups pendent from the polysaccharide backbone. This can alter the properties of the implant, and can result in greater access to enzymes that promote the degradation of the natural biodegradable polysaccharide.

Various synthetic schemes can be used for the preparation of a hydrophobic derivative of a natural biodegradable polysaccharide. In some modes of preparation, pendent polysaccharide hydroxyl groups are reacted with a compound that includes a hydrocarbon segment and a group that is reactive with the hydroxyl groups. This reaction can provide polysaccharide with pendent groups comprising hydrocarbon segments.

Any suitable chemical group can be coupled to the polysaccharide backbone and provide the polysaccharide with hydrophobic properties, wherein the polysaccharide becomes insoluble in water. Specifically, the pendent group can include one or more atoms selected from carbon (C), hydrogen (H), oxygen (O), nitrogen (N), and sulfur (S).

In some aspects, the pendent group includes a hydrocarbon segment that is a linear, branched, or cyclic $C_2$-$C_{18}$ group. More specifically the hydrocarbon segment includes a $C_2$-$C_{10}$, or a $C_4$-$C_8$, linear, branched, or cyclic group. The hydrocarbon segment can be saturated or unsaturated, and can include alkyl groups or aromatic groups, respectively. The hydrocarbon segment can be linked to the polysaccharide chain via a hydrolyzable bond or a non-hydrolyzable bond.

In some aspects the compound having a hydrocarbon segment that is reacted with the polysaccharide backbone is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. The hydroxyl group of a polysaccharide can be reacted with a fatty acid or anhydride to bond the hydrocarbon segment of the compound to the polysaccharide via an ester group.

The hydroxyl group of a polysaccharide can also cause the ring opening of lactones to provide pendent open-chain hydroxy esters. Exemplary lactones that can be reacted with the polysaccharide include caprolactone and glycolides.

Generally, if compounds having large hydrocarbon segments are used for the synthesis of the hydrophobic derivative, a smaller amount of the compound may be needed for its synthesis. For example, as a general rule, if a compound having a hydrocarbon segments with an alkyl chain length of $C_x$ is used to prepare a hydrophobic derivative with a DS of 1, a compound having a hydrocarbon segment with an alkyl chain length of $C_{(x\times2)}$ is reacted in an amount to provide a hydrophobic derivative with a DS of 0.5.

The hydrophobic derivative of the natural biodegradable polysaccharide can also be synthesized having combinations of pendent groups with two or more different hydrocarbon segments, respectively. For example, the hydrophobic derivative can be synthesized using compounds having hydrocarbon segments with different alkyl chain lengths. In one mode of practice, a polysaccharide is reacted with a mixture of two or more fatty acids (or derivatives thereof) selected from the group of acetic acid, propionic acid, butyric acid, isobutyric acid, valeric acid, caproic acid, caprylic acid, capric acid, and lauric acid to generate the hydrophobic derivative.

In other cases the hydrophobic derivative is synthesized having a non-hydrolyzable bond linking the hydrocarbon segment to the polysaccharide backbone. Exemplary non-hydrolyzable bonds include urethane bonds.

The hydrophobic derivative of the natural biodegradable polysaccharide can also be synthesized so that hydrocarbon segments are individually linked to the polysaccharide backbone via both hydrolyzable and non-hydrolyzable bonds. As another example, a hydrophobic derivative is prepared by reacting a mixture of butyric acid anhydride and butyl isocyanate with maltodextrin. This yields a hydrophobic derivative of maltodextrin with pendent butyric acid groups that are individually covalently bonded to the maltodextrin backbone with hydrolyzable ester linkages and non-hydrolyzable urethane linkages. The degradation of a coating having this type of hydrophobic derivative can occur by loss of the butyrate groups from hydrolysis of the ester linkages. However, a portion of the butyrate groups (the ones that are bonded via the urethane groups) are not removed from the polysaccharide backbone and therefore the natural biodegradable polysaccharide can maintain a desired degree of hydrophobicity, prior to enzymatic degradation of the polysaccharide backbone.

In some aspects, the group that is pendent from the polysaccharide backbone has properties of an active pharmaceutical ingredient (API). In this regard, the implants include polysaccharide-coupled API. In some aspects, an API which has a hydrocarbon segment can be hydrolyzed from the natural biodegradable polymer and released from the matrix to provide a therapeutic effect. One example of a therapeutically useful compound having a hydrocarbon segments is butyric acid, which has been shown to elicit tumor cell differentiation and apoptosis, and is thought to be useful for the treatment of cancer and other blood diseases.

Other illustrative compounds that include hydrocarbon segments include valproic acid and retinoic acid. These compounds can be coupled to a polysaccharide backbone to provide a pendent group, and then cleaved from the polysaccharide backbone upon degradation of the implant in vivo. Retinoic acid is known to possess antiproliferative effects and is thought to be useful for treatment of proliferative vitreoretinopathy (PVR). The pendent group that provides a therapeutic effect can also be a natural compound (such as butyric acid, valproic acid, and retinoic acid).

Another illustrative class of compounds that can be coupled to the polysaccharide backbone is the corticosteroids. An exemplary corticosteroid is triamcinolone. One method of coupling triamcinolone to a natural biodegradable polymer is by employing a modification of the method described in Cayanis, E. et al., Generation of an Auto-anti-idiotypic Antibody that Binds to Glucocorticoid Receptor, The Journal of Biol. Chem., 261(11): 5094-5103 (1986). Triamcinolone hexanoic acid is prepared by reaction of triamcinolone with ketohexanoic acid; an acid chloride of the resulting triamcinolone hexanoic acid can be formed and then reacted with the natural biodegradable polymer, such as maltodextrin or polyalditol, resulting in pendent triamcinolone groups coupled via ester bonds to the natural biodegradable polymer.

The hydrophobic derivative of the natural biodegradable polysaccharide can also be synthesized having two or more different pendent groups, wherein at least one of the pendent groups includes an API. The hydrophobic polysaccharide can be synthesized with an amount of a pendent groups including an API, that when released from the polysaccharide, provides a therapeutic effect to the subject. An example of such a hydrophobic derivative is maltodextrin-caproate-triamcinolone. This hydrophobic derivative can be prepared by reacting a mixture including triamcinolone hexanoic acid and an excess of caproic anhydride (n-hexanoic anhydride) with maltodextrin to provide a derivative with a DS of 2.5.

In some aspects, the group that is pendent from the polysaccharide includes a hydrocarbon segment that is an aromatic group, such as a phenyl group. As one example, o-acetylsalicylic acid is reacted with a polysaccharide such as maltodextrin to provide pendent chemical group having a hydrocarbon segment that is a phenyl group, and a non-hydrocarbon segment that is an acetate group wherein the pendent group is linked to the polysaccharide via an ester bond.

Additional features and descriptions of the biodegradable polymers that include the hydrophobic derivatives of natural biodegradable polysaccharides (referred to as Eureka™ SOLO polymers) can be found, for example, in U.S. Patent Publication Nos. 2007/0218102, 2007/0260054 and 2007/0224247, and references cited therein.

Applying the Coating

As an example, a biodegradable coating on the expandable and collapsible structure 12 can be made by preparing a coating composition including a biodegradable multiblock copolymer, such containing glycolic acid, caprolactone, and PEG polymeric blocks, dissolved in acetone at 30 mg/mL and applied by spraying the solution onto the structure (e.g., a balloon) (with or without a hydrogel base coat). Bioactive agent (e.g., in bioactive agent form) can be dissolved into the coating solution (1-50% by weight), or can be applied after the degradable coating is formed. For example, paclitaxel (dissolved in methanol, or present as bioactive agent in water) can be applied to the biodegradable coating.

The coating composition used to form the biodegradable coating can include one or more additional biocompatible polymers. For example, a secondary, tertiary, etc. biocompatible polymer can be included in the coating composition to form a coating with desired properties. The one or more additional polymers can increase the degradation of the coating. In some aspects, the biodegradable polymer is formed from a biodegradable polymer, such as polylactide, and a biocompatible polymer, such as one selected from the group consisting of poly(ethylene glycol) (PEG), poly(ethylene oxide), and poly(propylene oxide).

Various methods can be performed to associate the polymeric material and the bioactive agent with the surface of the expandable and collapsible structure. In many modes of practice, a coating composition including polymeric material and bioactive agent is prepared and then applied to the surface of the expandable and collapsible structure. In one mode of practice a coating composition is used including bioactive agent at a concentration in the range of about 10 mg/mL to about 50 mg/mL.

However, in some cases polymeric material can be applied to the surface independently of the bioactive agent. For example, a polymeric composition can be applied to the surface in a first step, and then in a second step a composition having bioactive agent (and without polymeric coating material) can be to the applied to the previously coated polymer. In one mode of practice a coating composition having bioactive agent at a concentration in the range of about 10 mg/mL to about 50 mg/mL (without polymeric coating material) is used. Additional, optional, steps can be performed to apply the same or other polymeric material, such as a topcoat, over the bioactive agent.

In one preferred aspect, a coating is formed on the surface of the expandable and collapsible structure using a spray coating process. In a particular mode of practice a balloon catheter is mounted on an apparatus that can manipulate the balloon for coating using a spray deposition process.

Further aspects and details of the balloon coating apparatus and method can be found in commonly owned provisional Application having Ser. No. 61/188,929, filed on Aug. 14, 2008, and entitled METHOD AND APPARATUS FOR COATING BALLOON CATHETERS (Chappa et al.), the disclosure of which is incorporated herein by reference.

Alternatively, a coating composition is dip-coated onto the surface of the expandable and collapsible structure to form a coated surface. In yet another method, the composition is brushed onto the surface of the expandable and collapsible structure. In some applications, the substrate can be subject to more than one step of coating with a mixture of polymeric material and bioactive agent, thereby allowing the formation of multiple layers on the substrate surface.

In some aspects, a coating is prepared by treating the coating materials that are disposed on the expandable and collapsible structure. For example, the coating composition can include a reactive group, that when activated, causes crosslinking of polymeric material and formation of the coating. The polymeric material used to form the coating can include pendent polymerizable groups, such as acrylate groups. The free radical polymerization of the polymerizable groups can be caused by the activation of a photoactivatable reagent that is a polymerization initiator. The applied composition can be treated with UV light to activate the polymerization initiator.

Particles of bioactive agent can be associated with the coating to provide partially embedded particles using a variety of techniques. In one technique a flexible hydrogel layer is formed on the surface of the expandable and collapsible structure. Next an aqueous composition containing bioactive agent is disposed on the surface of the flexible hydrogel layer. The water in the aqueous composition causes at least the surface of the flexible hydrogel layer to swell. The swelling makes the flexible hydrogel layer at least partially permeable to the bioactive agent deposited on the hydrogel layer, and bioactive agent move into the polymeric material of hydrogel layer. After a sufficient amount of time allowing for the bioactive agent to move partially into the hydrogel layer, water can then be removed, such as by evaporation, heating, or vacuum. Removal of water causes the hydrogel layer to shrink from a swollen state, physically constrain the bioactive agent, and results in the partial embedding of a substantial portion of the bioactive agent deposited on the surface of the hydrogel layer.

Figure 4:
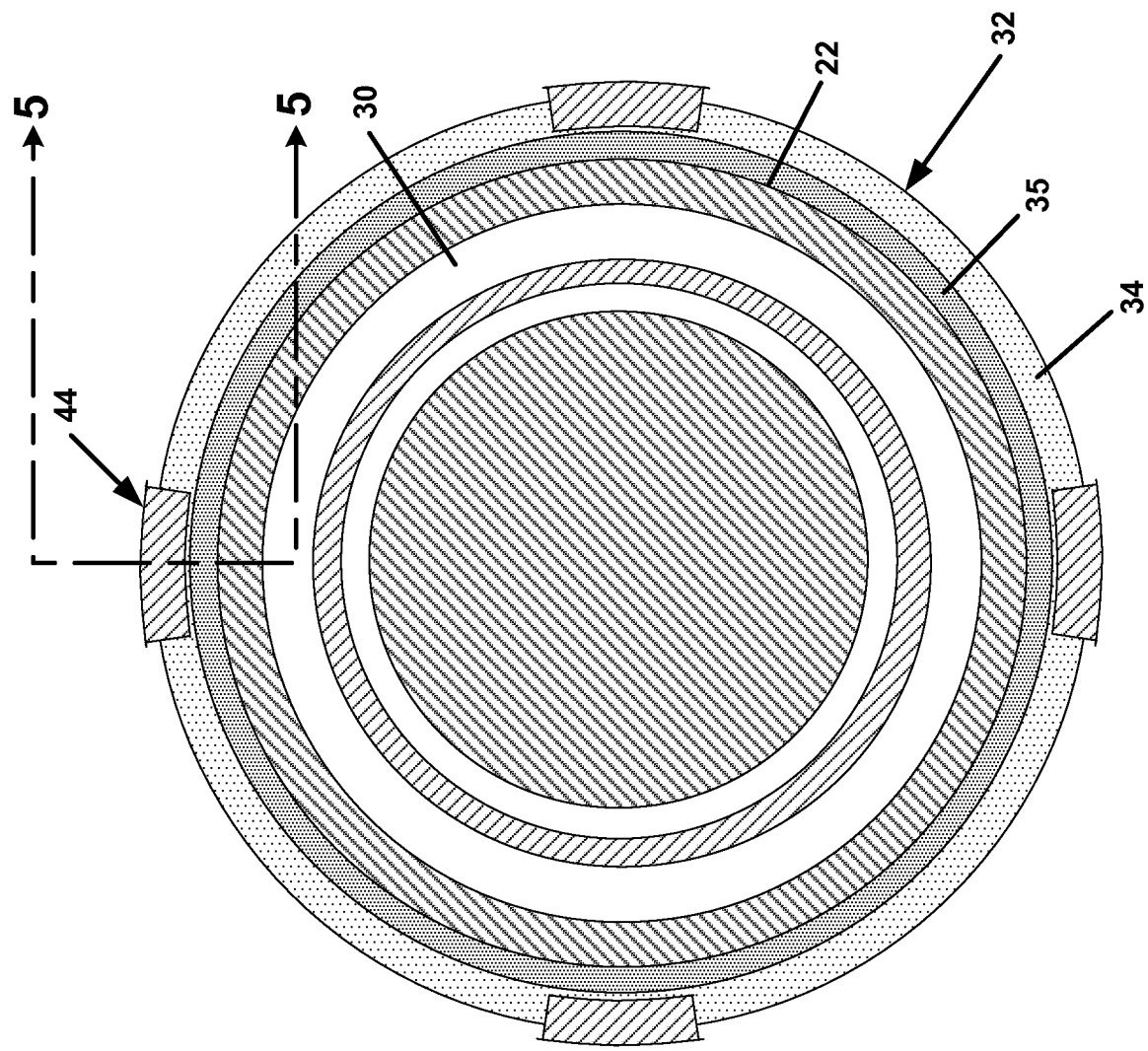
FIG. 4 is a cross-sectional view of the catheter assembly of FIG. 1 showing an optional protective layer.
Figure 5:
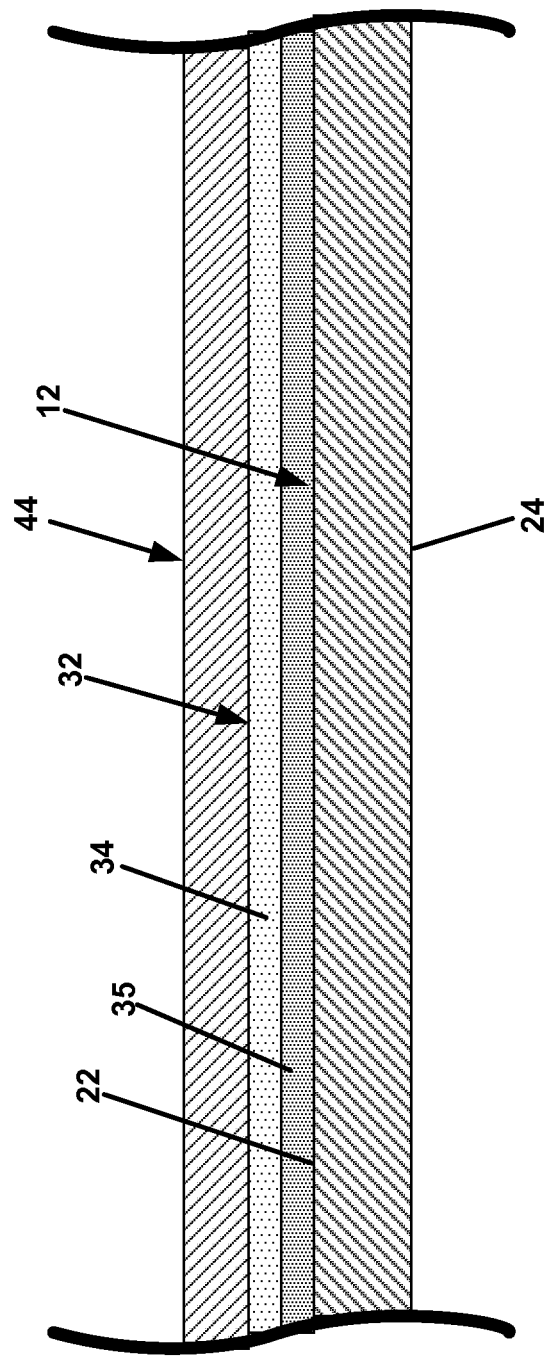
FIG. 5 is a cross-sectional view of the catheter assembly taken on line 5-5 of FIG. 4.

Referring now to FIGS. 4 and 5, the coating 32 of the catheter assembly is shown as having an optional release coating 35 disposed over the outer surface 22 of the expandable and collapsible structure 12. In the depicted embodiment, the optional release coating 35 is disposed between the outer surface 22 and the agent coating 34. In some embodiments, the optional release coating 35 need not occupy the entire region between the agent coating 34 and the expandable and collapsible structure 12.

The optional release coating 35 can be on the expandable and collapsible structure 12 and can promote release of the coating including the bioactive agent (the agent coating) from this structure at the target site. The release coating 35 can be between the agent coating 34 and the expandable and collapsible structure 12. The release coating 35 can be configured to promote release of the agent coating 34 at the target site within the subject. For example, the release coating 35 can swell and push against the drug containing coating. In an embodiment, it pushes against and fractures the drug containing coating. In an embodiment, the release coating includes or is made of a water swellable polymer that rapidly absorbs water. Upon exposure to blood, water wicks into the layer and reduces the adhesion between the release layer and the agent coating.

Figure 6:
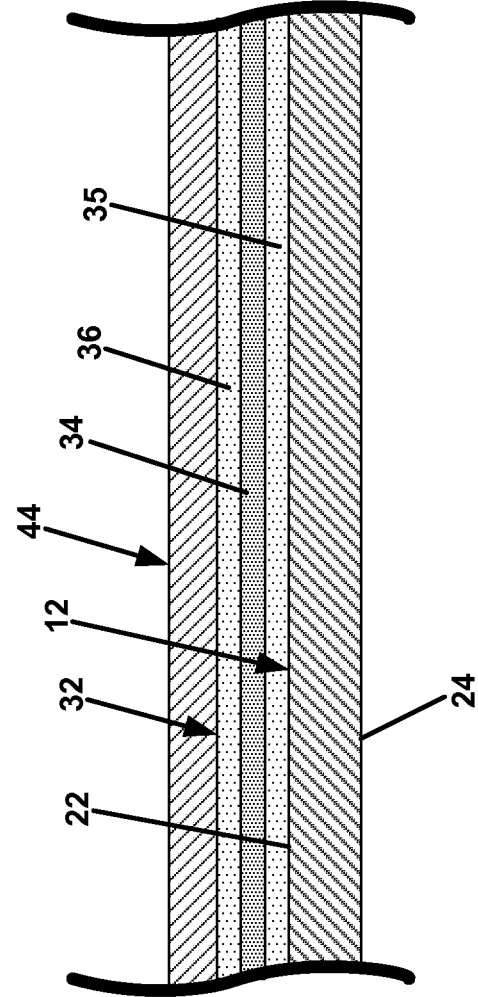
FIG. 6 is a cross-sectional view of the catheter assembly of FIG. 1 showing an optional release layer.

Referring now to FIG. 6, the coating 32 of the catheter assembly 10 is shown as having an optional protective layer 36 disposed over the agent coating 34. In one embodiment, the optional protective layer 36 is a lipid coating. In some embodiments, the protective layer 36 need not cover all of the agent coating 34.

The lipid coating can provide one or more of several advantageous characteristics to the catheter assembly 10. The lipid coating can, for example: 1) protect an underlying coating that includes a bioactive agent (e.g., the agent coating); 2) serve as a lubricant (e.g., a sacrificial lubricant) as the device contacts a subject's tissue; 3) provide a deformable hydrophobic matrix that further enhances delivery to a hydrophobic tissue or surface thereof (e.g., the walls of a blood vessel); 4) provide a matrix that maintains the structural integrity of the assembled coatings and bioactive agent beneath (e.g., hold things together); or more than one of these characteristics.

In an embodiment, the lipid coating is solid (e.g., waxy) or semi-solid at room temperature and soft or liquid at the body temperature of a subject. For example, the lipid coating can be or include a lipid or mixture of lipids that is solid at room temperature and liquid at 37° C. and forms a coating that protects an underlying coating including a bioactive agent. A mixture of 50 wt-% oleic acid and 50 wt-% dodecanoic acid is such a coating composition. In an embodiment, the present lipid coating can increase the amount of bioactive agent that is delivered to a tissue after a balloon catheter is put through a tortuous path.

In an embodiment, the lipid coating is solid at room temperature but softens or melts (e.g., liquefies) when exposed to the subject's body temperature. In an embodiment, the barrier layer is solid at room temperature but softens or melts as the coated portion of the device makes its way through the subject to the site at which the bioactive agent is to be delivered (the delivery site). For example, the barrier layer can be made of or include a composition that has a melting or softening point that is greater than room temperature and less than the subject's body temperature. The softening or melting can occur as the coated portion of the device makes its way to the delivery site, the melting or softening can occur at the delivery site, or both. The softening, softened, melting, or melted lipid composition can leave the catheter assembly 10, the portion of the catheter assembly 10 with the coating including the bioactive agent, or both as the coated portion of the device makes its way to the delivery site, at the delivery site, or both.

In an embodiment, the lipid coating can increase the amount of bioactive agent that is delivered to a desired location in a subject when the catheter assembly 10 is inserted into the subject. For example, the solid or semi-solid lipid coating can protect or isolate the coating including the bioactive agent during handling of the catheter assembly 10 outside the subject, as the coated portion of the device makes its way through the subject to the site at which the bioactive agent is to be delivered, or both. That is, the solid or semi-solid lipid coating can reduce the degree to which the coating including the bioactive agent is contacted by the atmosphere, by handling, by a guide catheter or other medical device, by tissue, by bodily fluids, or by a plurality thereof before the coated portion of the device arrives at the site at which the bioactive agent is to be delivered. This reduced contact can increase the amount of bioactive agent that is delivered at the desired site. Such a lipid coating has protected the underlying agent coating.

In an embodiment, the lipid coating increases the ease or reduces the resistance with which the catheter assembly 10 makes its way to the delivery site, for example, through a guide catheter. For example, the solid or semi-solid lipid coating can lubricate passage of the device as it is inserted into a guide catheter or other device, as the coated portion of the device makes its way through the guide catheter to the site at which the bioactive agent is to be delivered, or both. That is, the solid or semi-solid lipid coating can reduce the degree to which the coating including the bioactive agent contacts or rubs/abrades the guide catheter, the subject's tissue, bodily fluids, or both before the coated portion of the device arrives or is situated at the site at which the bioactive agent is to be delivered. The solid or semi-solid lipid coating can reduce friction from the device or the underlying coatings contacting a guide catheter, tissue, or fluid. Such lubricating can result in an increase the amount of bioactive agent that is delivered at the desired site. As the catheter assembly 10 makes its way to the delivery site, the lipid coating may be removed from the device as it lubricates. That is, the lipid coating can be a sacrificial lubricant.

In an embodiment, the lipid coating contacts the bioactive agent and the subject's tissue and aids in delivery of the agent to the tissue. The subject's tissue can have a degree of hydrophobicity that makes it more like the lipid coating composition than bodily fluids or the matrix making up the agent coating. The hydrophobicity of the lipid coating can aid absorption or adsorption of the bioactive agent into or onto the subject's tissue. In an embodiment, the bioactive agent may be in (e.g., dissolved or dispersed in) the lipid composition when it is at the delivery site. The lipid coating can adhere to the subject's tissue and also adhere bioactive agent (e.g., in the form of microparticles) to the subject's tissue. Such absorption, adsorption, or adhesion can result in an increase the amount of bioactive agent that is delivered at the desired site.

In an embodiment, the lipid coating increases the structural integrity of the coatings and bioactive agent on the device. For example, a solid or semisolid lipid coating can prevent or reduce the incidence of microparticles or portions of microparticles of active agent becoming dislodged from the device as it makes its way to the delivery site or as it is handled by medical personnel. The lipid coating can be viewed, for example, as a viscous matrix or an adhesive matrix that holds together these various coatings and particles as the catheter assembly 10 makes its way through a tortuous path to the delivery site. The lipid coating can be viewed, for example, as a viscous matrix or an adhesive matrix that holds together these various coatings and particles as the catheter assembly 10 contacts vessel walls or other tissue as it makes its way to the delivery site. As the catheter assembly 10 makes its way through the subject to the delivery site, the lipid coating may be removed from the device as it protects. That is, the lipid coating can serve as a sacrificial protectant.

The Lipid Composition

The present lipid composition can include a lipid or mixture of lipids. The lipid or mixture of lipids can, for example, be solid (e.g., waxy or paste-like) or semi-solid at room temperature and soft or liquid at the body temperature of a subject.

In an embodiment, the lipid composition includes a lipid with a melting point at or above 40° C. and a lipid with a melting point at or below 20° C. In an embodiment, the lipid composition includes a lipid with a melting point at or above 37° C. and a lipid with a melting point at or below 30° C. In an embodiment, the lipid composition includes a lipid with a melting point of about 35 to about 45° C. and a lipid with a melting point of about 0 to about 35° C.

Lipids that can be employed in the present lipid coating include: a marine oil, such as an oil from herring, menhaden, pilchard, sardine, whale, or a mixture thereof; soybean oil, cottonseed oil, corn oil, peanut oil, sunflower oil, safflower oil, olive oil, palm oil, or a mixture thereof; or mixtures thereof. The lipid composition can be a mixture of a lipid that is liquid at room temperature and a lipid that is solid at room temperature. A lipid that is liquid at room temperature is sold under the trade name High Oleic CV-65 canola oil (Cargill Inc., Minnetonka, Minn.). In an embodiment, the oils that are liquid at room temperature are not hydrogenated (e.g., neither partially hydrogenated nor fully hydrogenated). In an embodiment, the lipid that is solid at room temperature is an oil listed above that is partially or fully hydrogenated, for example, fully hydrogenated. A lipid that is liquid at room temperature is sold under the trade name STABLE FLAKE C® and is a cottonseed stearine product (C. & T. Refinery, Inc. of Richmond, Va.)

In certain embodiments, the lipid composition can include: an oil such as vegetable oil, flower oil, animal oil, marine oil (e.g., fish oil), tropical oil (e.g., coconut oil or palm oil), olive oil, peanut oil; lard, butterfat; a saturated fatty acid, for example, butanoic acid, hexanoic acid, octanoic acid, decanoic acid, dodecanoic acid, tetradecanoic acid, hexadecanoic acid, octadecanoic acid, or a mixture thereof; an unsaturated fatty acid, for example, octadecatrienoic acid, eicosanoic acid, eicosenoic acid, eicosatetraenoic acid, eicosapentaenoic acid, docosahexaenoic acid, palmitoleic acid, stearic acid, oleic acid, vaccenic acid, linoleic acid, alpha-linolenic acid, gamma-linolenic acid, behenic acid, erucic acid, lignoceric acid; a natural or synthetic phospholipids, for example, phosphatidylglycerol, phosphatidic acid, phosphatidylcholine, cardiolipin, phosphatidylethanolamine, phosphatidylserine, phosphatidylinositol, dimyristoylphosphatidylcholine, dioleoylphosphatidylcholine, dipalmitoylphosphatidylcholine, distearoylphosphatidylcholine; a mono-, di-, or triacylglycerol; or mixture thereof. Lard is rendered and clarified pork fat and melts around 86° F. (30° C.).

In certain embodiments, the present lipid composition can include one or more of a fat, a wax, a sterol, a phospholipid; a mono-, di-, or tri-glyceride; a fatty acyl, a glycerolipid, a glycerophospholipid, a sphingolipid (e.g., sphingomyelin), a saccharolipid, a polyketide, a sterol lipid, a prenol lipid, or a mixture thereof. Additional suitable lipids include a ceramide, a phosphosphingolipid, a glycosphingolipid, which can include fatty acid moieties that are saturated or mono-unsaturated with chain lengths from 16 to 26 carbon atoms.

The melting point of the present lipid composition can be determined by any one of a variety of art accepted methods. Suitable methods include the Mettler drop point test (see, e.g., ASTM D 3954). Briefly, in this test the sample to be measured is placed in a cup and heated at a given rate. The temperature at which a drop of molten material passes through a standard orifice is recorded. Other methods include the AOCS Method Cc 2-38 (the Wiley melting point), open capillary slip point, and the softening point tests.

Useful methods for making lipid compositions of that are or appear solid at room temperature and components of these compositions include those described in U.S. Pat. No. 6,544,579, which is incorporated herein by reference. The lipid composition can be cooled at ambient temperature or supercooled to provide the lipid coating.

In an embodiment, the lipid composition consists essentially of one or more lipids. In an embodiment, the lipid composition consists of one or more lipids. The lipid is generally not an active agent.

Fatty Acids

The present lipid composition can include one or more fatty acids, meaning free fatty acid not esterified or otherwise derivatized fatty acid. The fatty acid can include or be a salt of the carboxylic acid (e.g., a salt of the fatty acid). Suitable fatty acids include saturated and unsaturated fatty acids. Suitable unsaturated fatty acids include mono-unsaturated fatty acids and polyunsaturated fatty acids. In an embodiment, the fatty acid composition includes a mono-unsaturated fatty acid. In an embodiment, the fatty acid composition includes a saturated fatty acid. In an embodiment, the fatty acid composition includes a saturated fatty acid and a mono-unsaturated fatty acid.

Suitable saturated fatty acids include those including 6 to 28 carbon atoms. In an embodiment, the saturated fatty acid is of the formula $CH_3(CH_2)_n COOH$, where $4 \le n \le 18$. In certain embodiments, n is 4, 5, 6, 7, 8, 9, 10, 11, 12, 13, 14, 15, 16, 17, or 18. In certain embodiments, $6 \le n \le 8$, $8 \le n \le 6$, or $10 \le n \le 4$. In an embodiment, n is 10.

Suitable unsaturated fatty acids include those including 8 to 24 carbon atoms. In an embodiment, the unsaturated fatty acid is of the formula $CH_3(CH_2)_mC=CH(CH_2)_oCOOH$, m and o are independently greater than or equal to 2 and less than or equal to 18. In certain embodiments, m is 2, 3, 4, 5, 6, 7, 8, 9, 10, 11, 12, 13, 14, 15, 16, 17, or 18. In certain embodiments, o is 2, 3, 4, 5, 6, 7, 8, 9, 10, 11, 12, 13, 14, 15, 16, 17, or 18. In certain embodiments, $4 \le m \le 18$, $6 \le m \le 14$, or $6 \le m \le 8$. In certain embodiments, $4 \le o8$, $6 \le o \le 4$, or $6 \le o \le 8$. In an embodiment, m is 7, o is 11 and the double bond is cis. In an embodiment, the unsaturated fatty acid is of the formula $CH_2=CH(CH_2)_pCOOH$ with $3 \le p \le 21$.

In an embodiment, the unsaturated fatty acid can be described by C:D where C is the number of carbon atoms and D is the number of double bonds. C can be 6 to 24 and D can be 2 to 6. C and D are integers. In an embodiment, D can be 1 and C can be 6 to 24. The locations and stereochemistry of the double bond can be specified also.

In an embodiment, the fatty acid composition includes a saturated fatty acid with a melting point at or above 30° C. and an unsaturated fatty acid with a melting point at or below 20° C. In an embodiment, the fatty acid composition includes a saturated fatty acid with a melting point at or above 35° C. and an unsaturated fatty acid with a melting point at or below 35° C. In an embodiment, the fatty acid composition includes a saturated fatty acid with a melting point of about 30 to about 45° C. and an unsaturated fatty acid with a melting point of about 0 to about 35° C.

In an embodiment, the lipid coating includes or is made of a plurality of fatty acids. The plurality of fatty acids can be two fatty acids. The lipid coating can be a fatty acid or mixture of (e.g. two) fatty acids. The fatty acid or fatty acids can be a composition that is or that makes up the barrier layer. The plurality of fatty acids can be a mixture of fatty acids that are solid at room temperature and soft or liquid at body temperature of the subject. The plurality of fatty acids can be a mixture of fatty acids having a softening temperature greater than room temperature and less than body temperature of the subject. The plurality of fatty acids can be a mixture of fatty acids having a melting point greater than room temperature and less than body temperature of the subject.

Phospholipids

In an embodiment, the lipid composition includes a phospholipid. Suitable phospholipids include, for example, a phosphatidic acid, a phosphatidylcholine, a phosphatidylethanolamine, a phosphatidylserine, or mixture thereof.

Suitable phosphatidylcholines include, for example: 1,2-Didecanoyl-sn-glycero-3-phosphocholine (CAS no. 3436-44-0), 1,2-Dierucoyl-sn-glycero-3-phosphocholine (CAS no. 56649-39-9), 1,2-Dilinoleoyl-sn-glycero-3-phosphocholine (CAS no. 998-06-1), 1,2-Dilauroyl-sn-glycero-3-phosphocholine (CAS no. 18194-25-7), 1,2-Dimyristoyl-sn-glycero-3-phosphocholine (CAS no. 18194-24-6), 1,2-Dioleoyl-sn-glycero-3-phosphocholine (CAS no. 4235-95-4), 1,2-Dipalmitoyl-sn-glycero-3-phosphocholine (CAS no. 63-89-8), phosphatidylcholine purified from egg, phosphatidylcholine purified from soybean, lysophosphatidylcholine, 1-Myristoyl-2-palmitoyl-sn-glycero-3-phosphocholine, 1-Myristoyl-2-stearoyl-sn-glycero-3-phosphocholine, 1-Palmitoyl-2-myristoyl-sn-glycero-3-phosphocholine, 1-Palmitoyl-2-oleoyl-sn-glycero-3-phosphocholine (CAS no. 26853-31-6), 1,2-Distearoyl-sn-glycero-3-phosphocholine (CAS no. 816-94-4), 1-Palmitoyl-2-stearoyl-sn-glycero-3-phosphocholine, 1-Stearoyl-2-myristoyl-sn-glycero-3-phosphocholine, 1-Stearoyl-2-oleoyl-sn-glycero-3-phosphocholine, 1-Stearoyl-2-palmitoyl-sn-glycero-3-phosphocholine, or mixture thereof.

Suitable lysophosphatidylcholines include, for example: 1-Myristoyl-sn-glycero-3-phosphocholine (CAS no. 18194-24-6), 1-Palmitoyl-sn-glycero-3-phosphocholine (CAS no. 17364-16-8), 1-Stearoyl-sn-glycero-3-phosphocholine (CAS no. 19420-57-6), or mixture thereof.

Suitable phosphatidic acids include, for example: 1,2-Dierucoyl-sn-glycero-3-phosphate (Sodium Salt) (CAS no. 80724-31-8), 1,2-Dilauroyl-sn-glycero-3-phosphate (Sodium Salt), 1,2-Dimyristoyl-sn-glycero-3-phosphate (Sodium Salt) (CAS no. 80724-3), 1,2-Dioleoyl-sn-glycero-3-phosphate (Sodium Salt), 1,2-Dipalmitoyl-sn-glycero-3-phosphate (Sodium Salt) (CAS no. 71065-87-7), 1,2-Distearoyl-sn-glycero-3-phosphate (Sodium Salt) (CAS no. 108321-18-2), or mixture thereof.

Suitable phosphatidylethanolamines include, for example: 1,2-Dierucoyl-sn-glycero-3-phosphoethanolamine (CAS no. 988-07-2), 1,2-Dilauroyl-sn-glycero-3-phosphoethanolamine, 1,2-Dimyristoyl-sn-glycero-3-phosphoethanolamine (CAS no. 988-07-2), 1,2-Dioleoyl-sn-glycero-3-phosphoethanolamine, 1,2-Dipalmitoyl-sn-glycero-3-phosphoethanolamine (CAS no. 923-61-5), 1-Palmitoyl-2-oleoyl-sn-glycero-3-phosphoethanolamine, 1,2-Distearoyl-sn-glycero-3-phosphoethanolamine (CAS no. 1069-79-0), or mixture thereof.

Suitable phosphatidylserines include, for example: 1,2-Dilauroyl-sn-glycero-3-phosphoserine (Sodium Salt), 1,2-Dimyristoyl-sn-glycero-3-phosphoserine (Sodium Salt), 1,2-Dipalmitoyl-sn-glycero-3-phosphoserine (Sodium Salt), 1,2-Distearoyl-sn-glycero-3-phosphoserine (Sodium Salt), 1,2-Dioleoyl-sn-glycero-3-phosphoserine (Sodium Salt) (CAS no. 70614-14-1), or mixture thereof.

Figure 7:
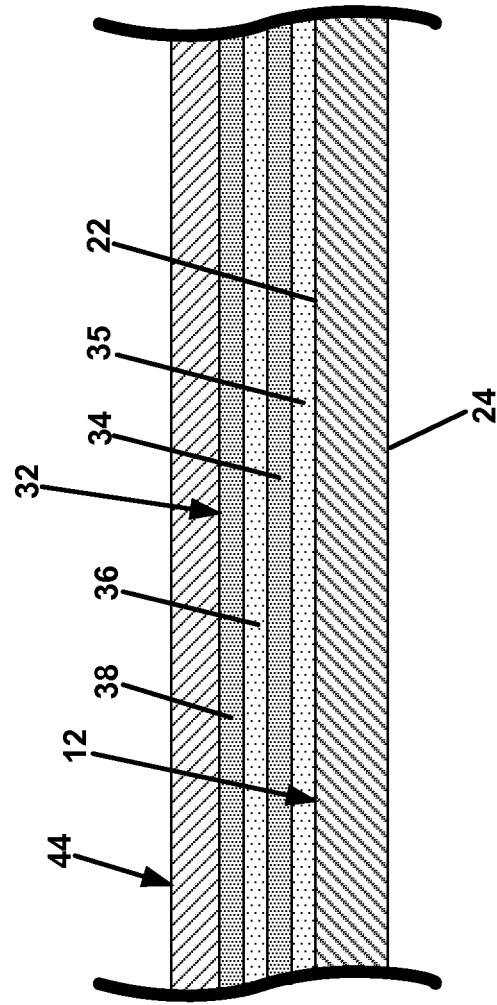
FIG. 7 is a cross-sectional view of the catheter assembly of FIG. 1 showing an optional second protective layer.

Referring now to FIG. 7, the coating 32 of the catheter assembly 10 is shown having an optional second protective layer 38 disposed over the protective layer 36. In one embodiment, the optional second protective layer 38 is the same as the protective layer 36. In another embodiment, the optional second protective layer 38 is different than the protective layer 36.

Referring now to FIGS. 1 and 2, the sleeve 14 will be described. The sleeve 14 is disposed over the outer surface 22 of the expandable and collapsible structure 12. The sleeve 14 is adapted to expand from a compressed shape (shown in FIG. 1) and an enlarged shape (shown in FIG. 14) and to collapse from the enlarged shape to the compressed shape. The sleeve 14 is adapted to protect the coating disposed on the outer surface 22 of the expandable and collapsible structure 12 as the catheter assembly 10 is guided along the guide wire 28 to the target site.

The sleeve 14 is manufactured from a shape memory alloy. A shape memory alloy is one that can be deformed from an original shape and return to that original shape from the deformed shape under certain conditions (e.g., temperatures). In the depicted embodiment, the original shape of the sleeve 14 is the compressed state. As the compressed state is the original shape, the sleeve 14 returns to the compressed state after expansion when the temperature of the sleeve 14 reaches a first temperature. In one embodiment, the first temperature is less than or equal to about normal body temperature (i.e., 37 deg C.). In another embodiment, the first temperature is greater than or equal to about normal body temperature.

In the depicted embodiment, the shape memory alloy of the sleeve 14 is a nickel-titanium (Ni—Ti) alloy (e.g., nitinol). In another embodiment, the shape memory alloy can be Ni—Ti—X, Cu—Ni—Al, Cu—Zn—Al, Fe—Mn—Si, Ni—Ti—Co, Ni—Cu—X, Ni—Al, etc.

The sleeve 14 includes a body 39 having a first axial end 40 and an oppositely disposed second axial end 42. The first axial end 40 is disposed adjacent to the distal end 16 of the expandable and collapsible structure 12 while the second axial end 42 is disposed adjacent to the proximal end 18 of the expandable and collapsible structure 12.

In the depicted embodiment, the body 39 of the sleeve 14 includes a plurality of rails 44 and a plurality of ribs 46. In one embodiment, the body 39 includes at least two rails 44. In another embodiment, the body 39 includes at least four rails 44. In another embodiment, the body 39 includes at least eight rails 44. In another embodiment, the body 39 includes at least twelve rails 44.

In the depicted embodiment of FIG. 1, the rails 44 extend in a generally longitudinal direction between the first and second axial ends 40, 42. In FIG. 1, the rails 44 are arranged in the sleeve 14 so that the rails 44 are generally parallel when the sleeve 14 is in the compressed state.

In the depicted embodiment, each of the rails 44 includes a first end 48 and an oppositely disposed second end 50. The first end 48 is disposed adjacent to the distal end 16 of the expandable and collapsible structure 12 while the second end 50 is disposed adjacent to the proximal end 18 of the expandable and collapsible structure 12. In the depicted embodiment, the first ends 48 of adjacent rails 44 are connectedly engaged while the second ends 50 of the rails 44 are connectedly engaged. In one embodiment, the first ends 48 of adjacent rails 44 are monolithic.

The ribs 46 extend between the rails 44. The ribs 46 are adapted to provide support to the rails 44. Each of the ribs 46 includes a first end portion 52 and an oppositely disposed second end portion 54. The first end portion 52 is engaged to a first rail 44a of the plurality of rails 44 while the second end portion 54 is engaged to a second rail 44b of the plurality of rails 44. In the depicted embodiment, the first and second rails 44a, 44b are immediately adjacent. In one embodiment, the rails 44 and the ribs 46 are integral. In another embodiment, the rails 44 and the ribs 46 are monolithic. In the depicted embodiment of FIG. 1, the ribs 46 are disposed at an oblique angle relative to the rails 44 when the sleeve 14 is in the enlarged state.

The rails 44 and ribs 46 of the sleeve 14 include an exterior surface 55 and an interior surface 56. The interior surface 56 defines a bore 58 in which the expandable and collapsible structure 12 is disposed. The rails 44 have a first thickness that is measured between the exterior surface 55 and the interior surface 56 while the ribs 46 have a second thickness. In one embodiment, the first and second thicknesses are about equal. In another embodiment, the first thickness is greater than the second thickness. In one embodiment, the first thickness is in a range of about 50 µm to about 1 mm. In another embodiment, the first thickness is in a range of about 100 µm to about 200 µm.

Figure 8:
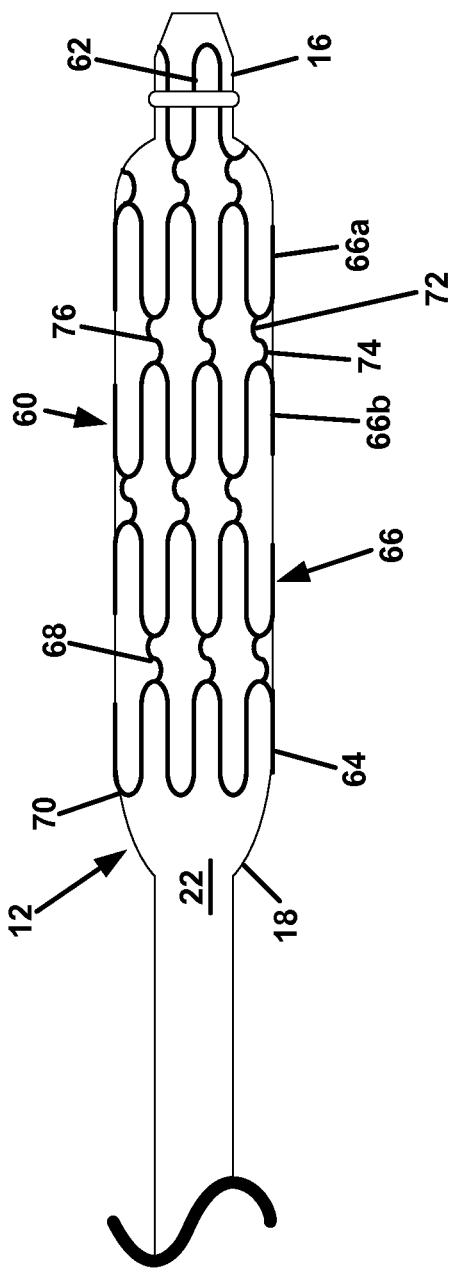
FIG. 8 is a side view of an alternate embodiment of a sleeve of the catheter assembly.

Referring now to FIG. 8, an alternate embodiment of a sleeve 60 is shown. The sleeve 60 is disposed over the outer surface 22 of the expandable and collapsible structure 12. The sleeve 60 includes a first axial end 62 and an oppositely disposed second axial end 64. The sleeve 60 further includes a plurality of rails 66 and a plurality of ribs 68.

In the depicted embodiment of FIG. 8, the plurality of rails 66 is disposed between the first and second axial ends 62, 64. Each of the rails 66 is wrapped around the outer surface 22 of the expandable and collapsible structure 12 so that each of the rails 66 has a generally annular shape.

Each of the rails 66 includes an undulation 70. In the depicted embodiment, each of the rails 66 includes a plurality of undulations 70. The undulation 70 is generally wave shaped. The undulation 70 is adapted to decrease as the sleeve 60 expands to the enlarged state. In the depicted embodiment, the undulation 70 is sinusoidal in shape.

The ribs 68 extend between the rails 66. In the depicted embodiment, the ribs 68 are disposed in a generally longitudinal direction. Each of the ribs 68 includes a first end portion 72 and an oppositely disposed second end portion 74. The first end portion 72 is engaged to a first rail 66a of the plurality of rails 66 while the second end portion 74 is engaged to a second rail 66b of the plurality of rails 66. In the depicted embodiment, the first and second rails 66a, 66b are immediately adjacent. In one embodiment, the rails 66 and the ribs 68 are integral. In another embodiment, the rails 66 and the ribs 68 are monolithic.

In the depicted embodiment, the ribs 68 include an undulation 76. The undulation 76 is adapted to allow the rib 68 to expand as the sleeve 60 is enlarged. The undulation 76 is generally wave shaped. In the depicted embodiment, the undulation is sinusoidal in shape.

Figure 9:
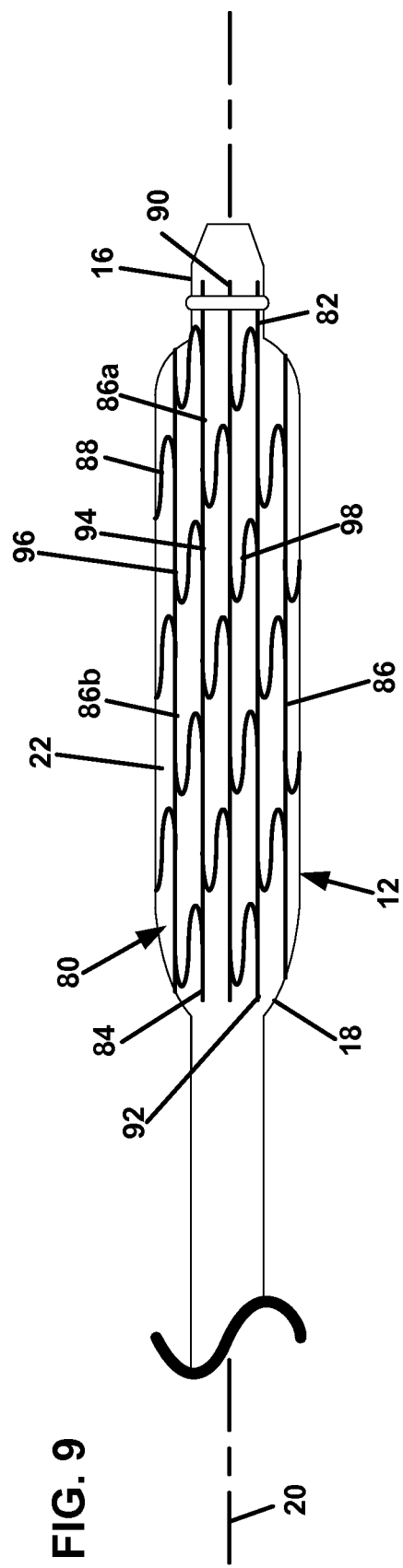
FIG. 9 is a side view of an alternate embodiment of a sleeve of the catheter assembly.

Referring now to FIG. 9, an alternate embodiment of a sleeve 80 is shown. The sleeve 80 is disposed over the outer surface 22 of the expandable and collapsible structure 12. The sleeve 80 includes a first axial end 82 and an oppositely disposed second axial end 84. The first axial end 82 is disposed adjacent to the distal end 16 of the expandable and collapsible structure 12 while the second axial end 84 is disposed adjacent to the proximal end 18 of the expandable and collapsible structure 12.

The sleeve 80 further includes a plurality of rails 86 and a plurality of ribs 88. In the depicted embodiment of FIG. 9, the rails 86 extend in a generally longitudinal direction between the first and second axial ends 82, 84. In FIG. 9, the rails 86 are arranged in the sleeve 80 so that the rails 86 are generally parallel when the sleeve 80 is in the compressed state.

In the depicted embodiment, each of the rails 86 includes a first end 90 and an oppositely disposed second end 92. The first end 90 is disposed adjacent to the distal end 16 of the expandable and collapsible structure 12 while the second end 92 is disposed adjacent to the proximal end 18 of the expandable and collapsible structure 12.

The ribs 88 extend between the rails 86. In the depicted embodiment, the ribs 88 are disposed in a generally direction that is generally perpendicular to the longitudinal axis 20. Each of the ribs 88 includes a first end portion 94 and an oppositely disposed second end portion 96. The first end portion 94 is engaged to a first rail 86a of the plurality of rails 86 while the second end portion 96 is engaged to a second rail 86b of the plurality of rails 86. In the depicted embodiment, the first and second rails 86a, 86b are immediately adjacent. In one embodiment, the rails 86 and the ribs 88 are integral. In another embodiment, the rails 86 and the ribs 88 are monolithic.

In the depicted embodiment, the ribs 88 include an undulation 98. The undulation 98 is adapted to allow the rib 88 to expand as the sleeve 80 is enlarged. The undulation 98 is generally wave shaped. In the depicted embodiment, the undulation 98 is sinusoidal in shape.

Figure 10:
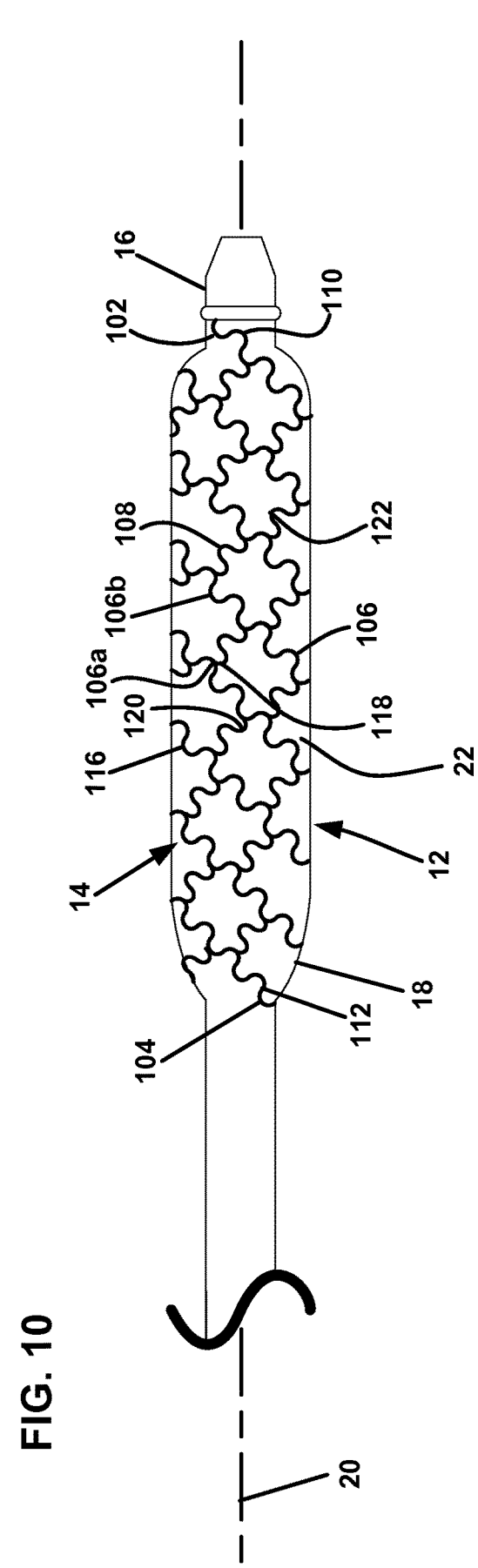
FIG. 10 is a side view of an alternate embodiment of a sleeve of the catheter assembly.

Referring now to FIG. 10, an alternate embodiment of a sleeve 100 is shown. The sleeve 100 is disposed over the outer surface 22 of the expandable and collapsible structure 12. The sleeve 100 includes a first axial end 102 and an oppositely disposed second axial end 104. The first axial end 102 is disposed adjacent to the distal end 16 of the expandable and collapsible structure 12 while the second axial end 104 is disposed adjacent to the proximal end 18 of the expandable and collapsible structure 12.

The sleeve 100 further includes a plurality of rails 106 and a plurality of ribs 108. In the depicted embodiment, each of the rails 106 includes a first end 110 and an oppositely disposed second end 112. The first end 110 is disposed adjacent to the distal end 16 of the expandable and collapsible structure 12 while the second end 112 is disposed adjacent to the proximal end 18 of the expandable and collapsible structure 12. Each of the rails 106 is wrapped about the outer surface 22 of the expandable and collapsible structure 12 so that each of the rails 106 spirals about the longitudinal axis 20 of the expandable and collapsible structure 12.

In the depicted embodiment, each of the rails 106 includes an undulation 116 so that a length of each of the rails 106 can extend as the sleeve 100 is enlarged. In the depicted embodiment, each of the rails 106 includes a plurality of undulations 116. The undulation 116 is generally wave shaped. The undulation 116 is adapted to decrease as the sleeve 100 expands to the enlarged state. In the depicted embodiment, the undulation 116 is sinusoidal in shape.

The ribs 108 extend between the rails 106. Each of the ribs 108 includes a first end portion 118 and an oppositely disposed second end portion 120. The first end portion 118 is engaged to a first rail 106a of the plurality of rails 106 while the second end portion 120 is engaged to a second rail 106b of the plurality of rails 106. In the depicted embodiment, the first and second rails 106a, 106b are immediately adjacent. In one embodiment, the rails 106 and the ribs 108 are integral. In another embodiment, the rails 106 and the ribs 108 are monolithic. In the depicted embodiment, the ribs 108 are generally perpendicular to the rails 106 when the sleeve 100 is in the compressed state.

In the depicted embodiment, the ribs 108 include an undulation 122. The undulation 122 is adapted to allow the rib 108 to expand as the sleeve 100 is enlarged. The undulation 122 is generally wave shaped. In the depicted embodiment, the undulation 122 is sinusoidal in shape.

Referring now to FIG. 1, the engagement of the sleeve 14 and the expandable and collapsible structure 12 will be described. The sleeve 14 is disposed about the expandable and collapsible structure 12 so that the first axial end 40 is disposed adjacent to the distal end 16 of the expandable and collapsible structure 12 and the second axial end 42 is disposed adjacent to the proximal end 18 of the expandable and collapsible structure 12. In one embodiment, the first axial end 40 of the sleeve 14 is secured (e.g., glued, bonded, fused, mechanically fastened, and combinations thereof) to the distal end 16 of the expandable and collapsible structure 12 while the second axial end 42 of the sleeve 14 is unsecured from the proximal end 18 of the expandable and collapsible structure 12.

In the depicted embodiment of FIG. 1, the first axial end 40 of the sleeve 14 is mechanical secured to the distal end 16 of the expandable and collapsible structure 12. In the depicted embodiment of FIG. 1, the first axial end 40 of the sleeve 14 is mechanically secured to the distal end 16 by a band 130a. The band 130a can be crimped about the distal end 16 with the first axial end 40 of the sleeve 14 disposed between the band 130a and the distal end 16 of the expandable and collapsible structure 12. In another embodiment, the band 130a is shrink-wrap tubing that has an inner diameter that decreases upon application of heat. In another embodiment, the first axial end 40 is bonded to the distal end 16 of the expandable and collapsible structure 12 with an adhesive. In another embodiment, the first axial end 40 is mechanically secured and adhesively bonded to the distal end 16 of the expandable and collapsible structure 12.

Figure 11:
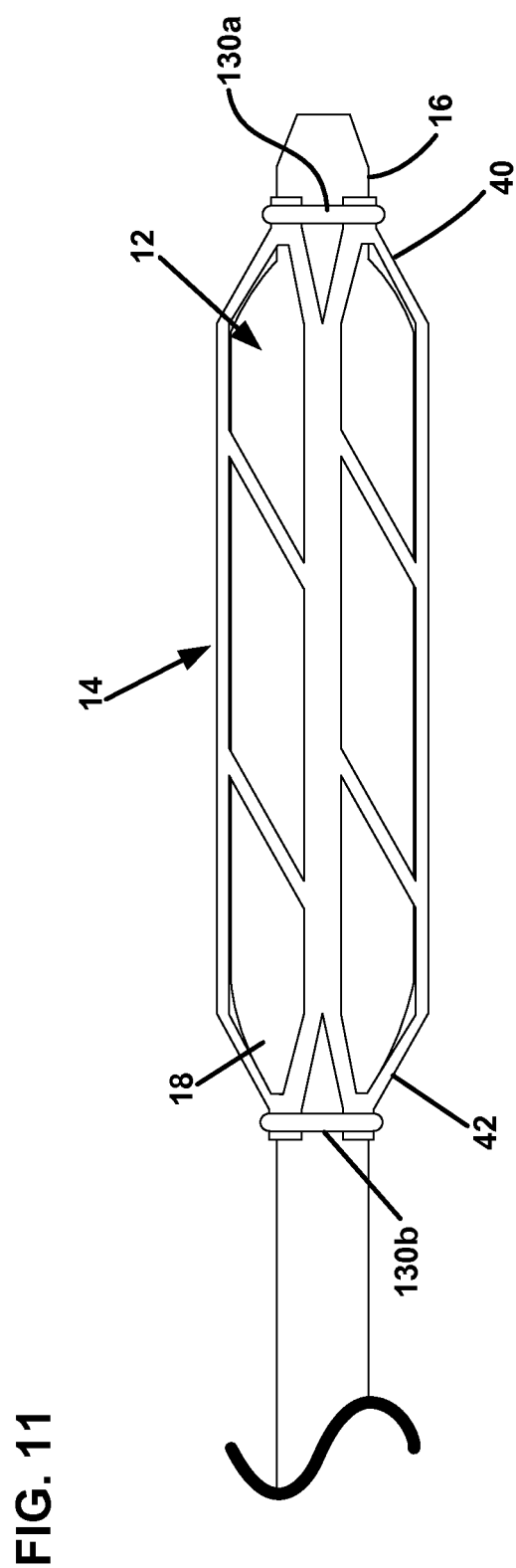
FIG. 11 is a side view of the catheter assembly showing an alternate engagement arrangement between the expandable and collapsible structure and the sleeve.

Referring now to FIG. 11, an alternate embodiment of the catheter assembly 10 is shown in which the first and second axial ends 40, 42 of the sleeve 14 are secured (e.g., glued, bonded, fused, mechanically fastened, and combinations thereof) to the distal and proximal ends 16, 18 of the expandable and collapsible structure 12, respectively. In the depicted embodiment of FIG. 11, the first and second axial ends 40, 42 of the sleeve 14 are mechanically secured to the distal and proximal ends 16, 18, respectively, of the expandable and collapsible structure 12. The first axial end 40 of the sleeve 14 is secured to the distal end 16 by the band 130a while the second axial end 42 of the sleeve 14 is secured to the proximal end 18 by a second band 130b. In one embodiment, adhesive is disposed between the band 130a and the distal end 16 and between the second band 130b and the proximal end 18.

Figure 12:
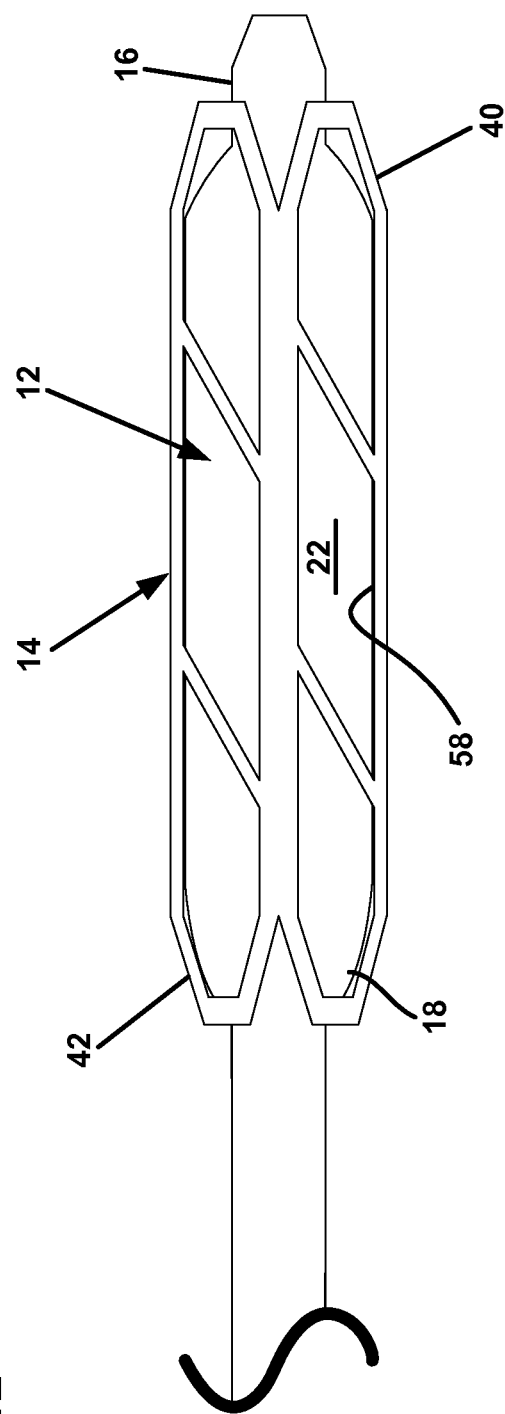
FIG. 12 is a side view of the catheter assembly showing an alternate engagement arrangement between the expandable and collapsible structure and the sleeve.

Referring now to FIG. 12, an alternate embodiment of the catheter assembly 10 is shown. In this embodiment, the first and second axial ends 40, 42 of the sleeve 14 are unsecured from the distal and proximal ends 16, 18 of the expandable and collapsible structure 12. In this embodiment, an inner diameter of the bore 58 of the sleeve 14 when the sleeve 14 is in the compressed state is less than an outer diameter of the outer surface 22 of the expandable and collapsible structure 12 when the expandable and collapsible structure 12 is in the contracted state. This interference fit between the expandable and collapsible structure 12 and the sleeve 14 retains the sleeve 14 about the expandable and collapsible structure 12.

Figure 13:
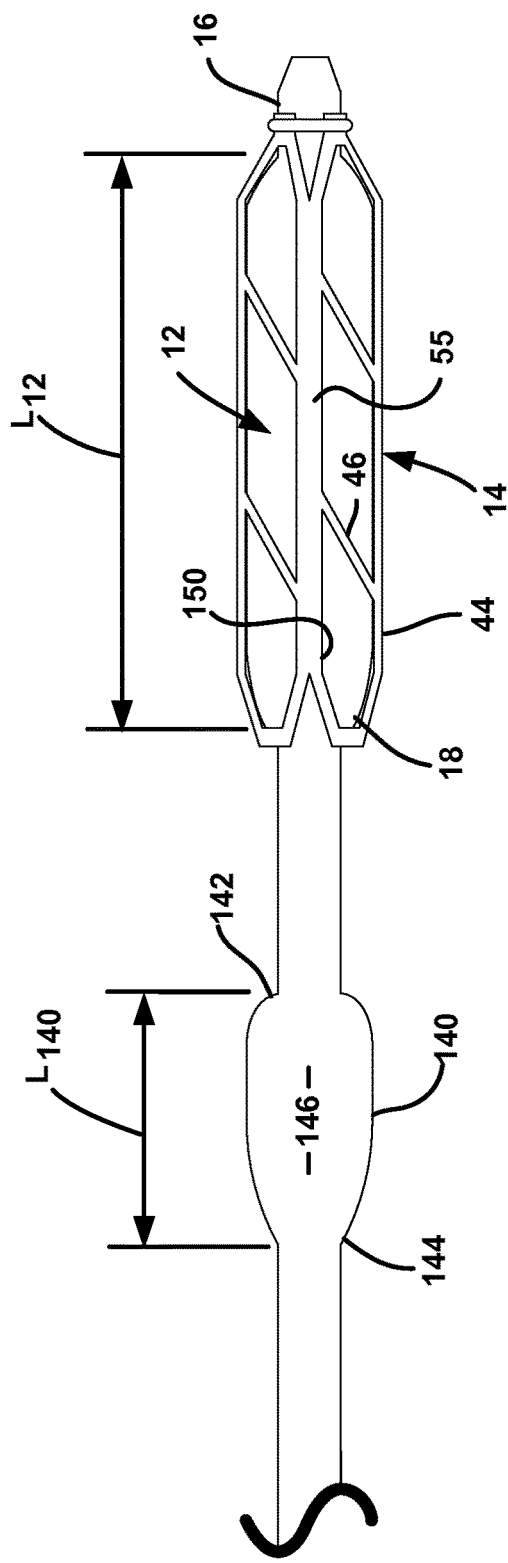
FIG. 13 is a side view of the catheter assembly showing a second expandable and collapsible structure.

Referring now to FIG. 13, the catheter assembly 10 is shown with a second expandable and collapsible structure 140. The second expandable and collapsible structure 140 is disposed adjacent to the proximal end 18 of the expandable and collapsible structure 12. The second expandable and collapsible structure 140 is adapted to expand from a contracted state (shown in FIG. 13) to a dilated state (shown in FIG. 18) and to contract from the dilated state to the contracted state.

The second expandable and collapsible structure 140 is adapted to decrease or prevent the flow of blood through a blood vessel of the body of the patient as the expandable and collapsible structure 12 is being dilated. The second expandable and collapsible structure 140 includes a first end 142, an oppositely disposed second end 144 and an outer surface 146 that extends between the first and second ends 142, 144. In the depicted embodiment, a length $L_{140}$ of the second expandable and collapsible structure 140 is less than a length $L_{12}$ of the expandable and collapsible structure 12 when the expandable and collapsible structure 12 and the second expandable and collapsible structure 140 are in the contracted state.

Referring now to FIGS. 1, 2, 13, the plurality of rails 44 and the plurality of ribs 46 of the sleeve 14 define a plurality of openings 150 that extend through the exterior and interior surfaces 55, 56 of the sleeve 14. The plurality of openings 150 is substantially open when the sleeve 14 is in the compressed state. In one embodiment, the plurality of openings 150 define an area at the exterior surface 55 of the sleeve 14 that is greater than about 40% of a total surface area (i.e., total surface area=surface area of the rails 44 at the exterior surface 55+surface area of the ribs 46 at the exterior surface 55+area of the openings 150 at the exterior surface 55) of the exterior surface 55 of the sleeve 14 when the sleeve 14 is in the compressed state. In another embodiment, the plurality of openings 150 define an area at the exterior surface 55 of the sleeve 14 that is greater than or equal to about 50% of the total surface area of the exterior surface 55 of the sleeve 14 when the sleeve 14 is in the compressed state. In another embodiment, the plurality of openings 150 define an area at the exterior surface 55 of the sleeve 14 that is greater than or equal to about 60% of the total surface area of the exterior surface 55 of the sleeve 14 when the sleeve 14 is in the compressed state. In another embodiment, the plurality of openings 150 define an area at the exterior surface 55 of the sleeve 14 that is greater than or equal to about 70% of the total surface area of the exterior surface 55 of the sleeve 14 when the sleeve 14 is in the compressed state. In another embodiment, the plurality of openings 150 define an area at the exterior surface 55 of the sleeve 14 that is in a range of about 40% to about 95% of the total surface area of the exterior surface 55 of the sleeve 14 when the sleeve 14 is in the compressed state.

The coating 32 of the expandable and collapsible structure 12 primarily resides in the openings 150 of the sleeve 14. It will be understood that the term "primarily" allows for some of the coating 32 to be disposed between the rails 44 and the outer surface 22 of the expandable and collapsible structure 12 and between the ribs 46 and the outer surface 22 of the expandable and collapsible structure 12. As the coating 32 primarily resides between the openings 150 of the sleeve 14, the size of the openings 150 and the first thickness of the rails 44 cooperatively define an amount of coating 32 that can be carried by the catheter assembly 10 to the target site. In the subject embodiment, an outer diameter of the coating 32 is less than an outer diameter of the sleeve 14 when the expandable and collapsible structure 12 is in the contracted state and the sleeve 14 is in the compressed state. As the first thickness of the rails 44 increases, the thickness of the coating 32 can increase.

Figure 14:
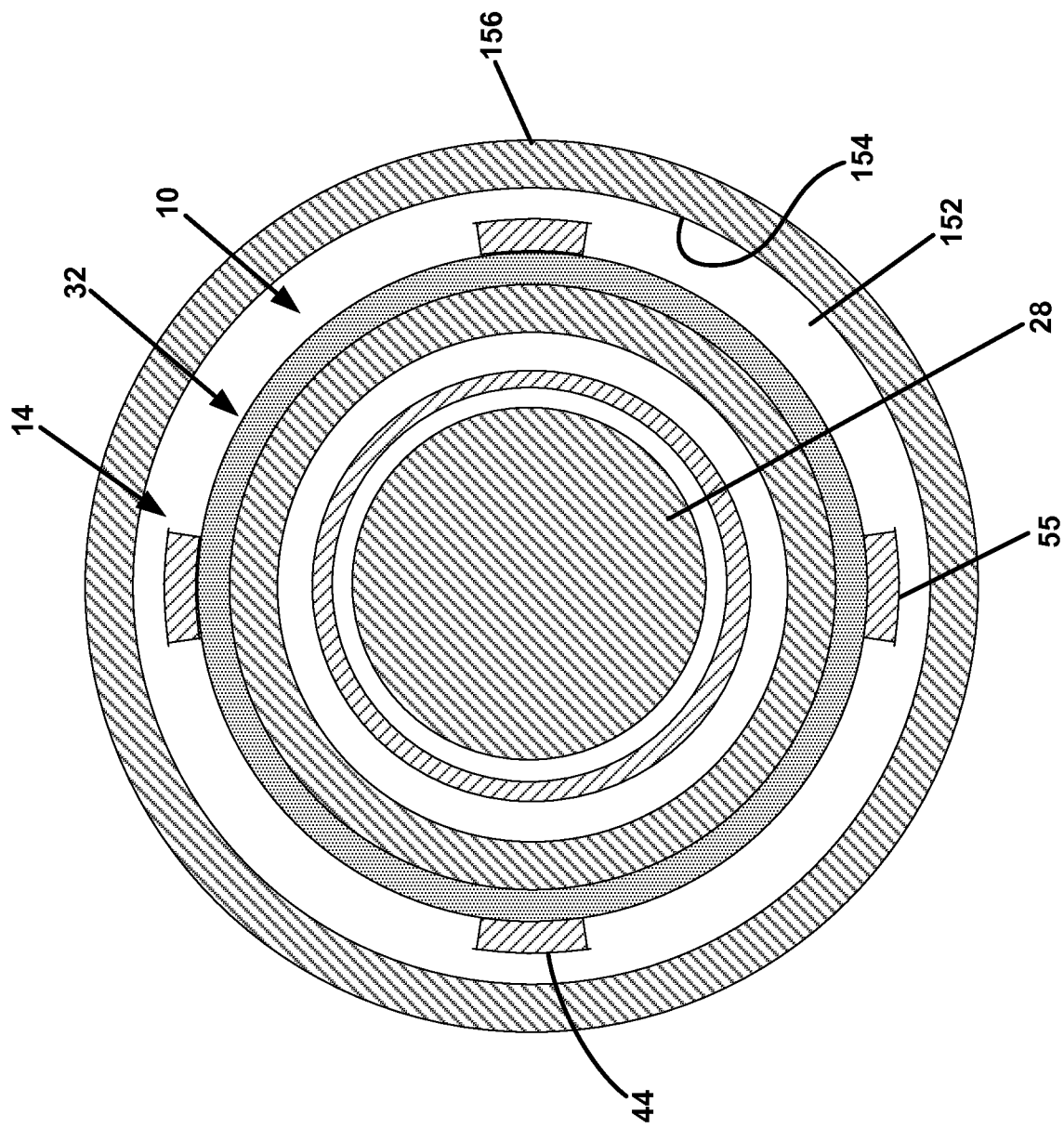
FIG. 14 is a side view of the catheter assembly with the expandable and collapsible structure in the dilated state and the sleeve in the enlarged state.
Figure 15:
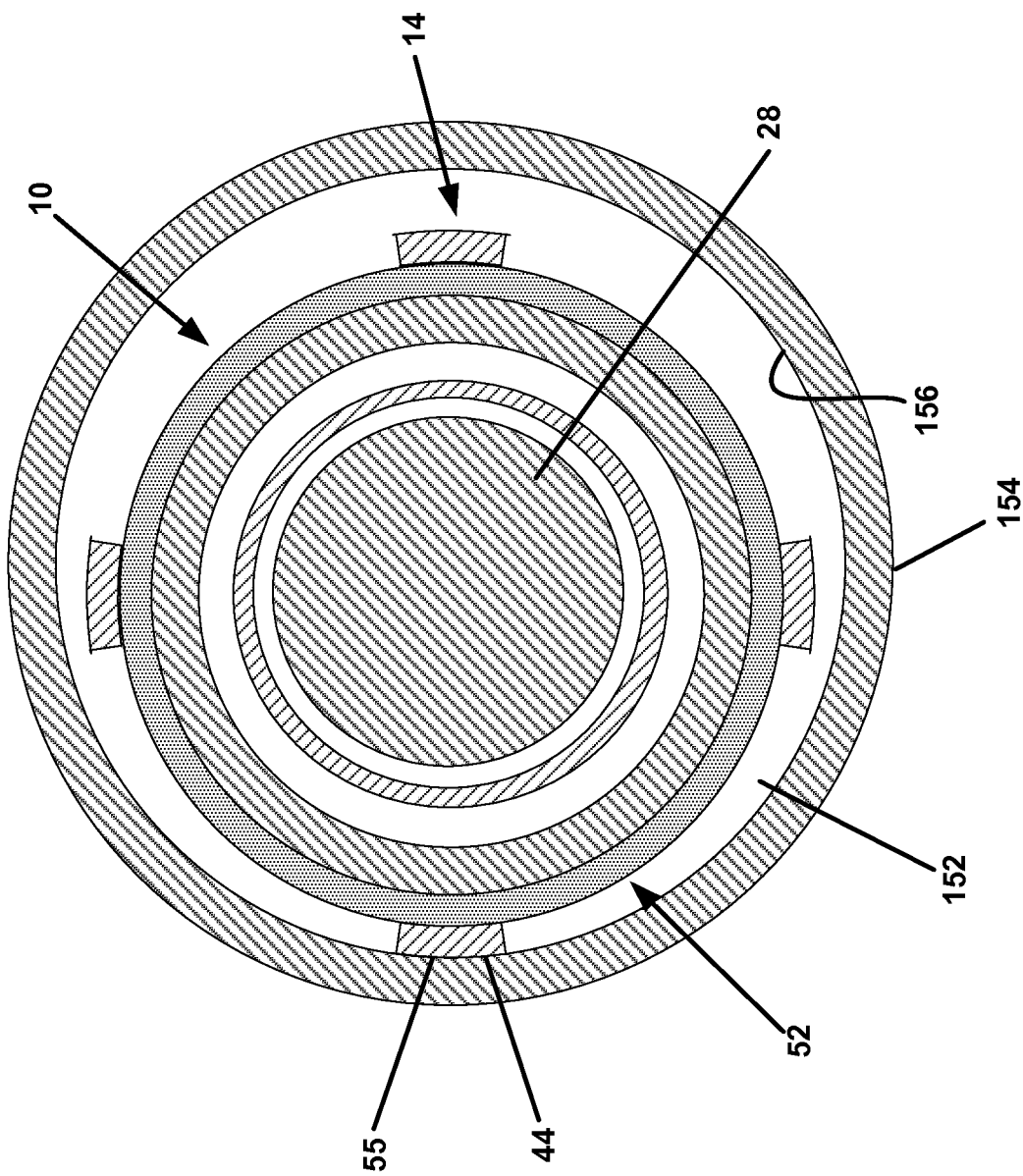
FIG. 15 is a cross-sectional view of the catheter assembly taken on line 15-15 of FIG. 14.
Figure 16:
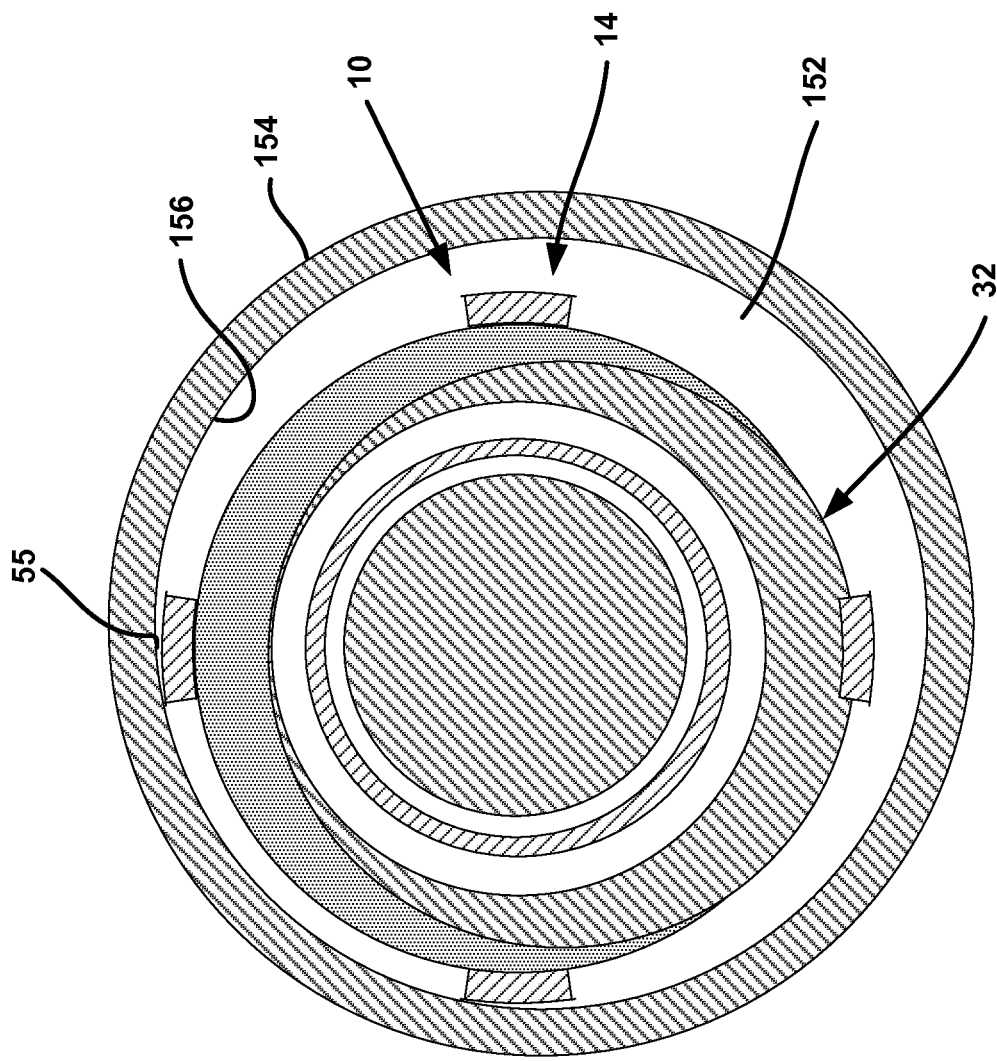
FIG. 16 is a cross-sectional view of the catheter assembly disposed in a guide tube.

Referring now to FIGS. 14-16, the catheter assembly 10 is guided along the guide wire 28 to the target site in the body of the patient. As the catheter assembly 10 is guided along the guide wire 28, the catheter assembly 10 is disposed in an inner bore 152 of a guide tube 154.

As best shown in FIGS. 15 and 16, the catheter assembly 10 may contact an inner wall 156 of the guide tube 154 as the catheter assembly 10 is guided to the target site. The sleeve 14 is adapted to protect the coating 32 of the catheter assembly 10 as the catheter assembly 10 travels to the target site. As the outer diameter of the rails 44 of the sleeve 14 is greater than the outer diameter of the coating 32 when the sleeve 14 is in the compressed state, the rails 44 of the sleeve 14 prevent or reduce the amount of direct contact between the coating 32 and the inner wall 156. As the catheter assembly 10 travels to the target site, the inner wall 156 of the guide tube 154 contacts the exterior surfaces 55 of the rails 44 rather than the coating 32. As the direct contact between the catheter assembly 10 and the guide tube 154, more of the coating 32 is available for delivery at the target site since less of the coating is lost during transportation to the target site.

Figure 17:
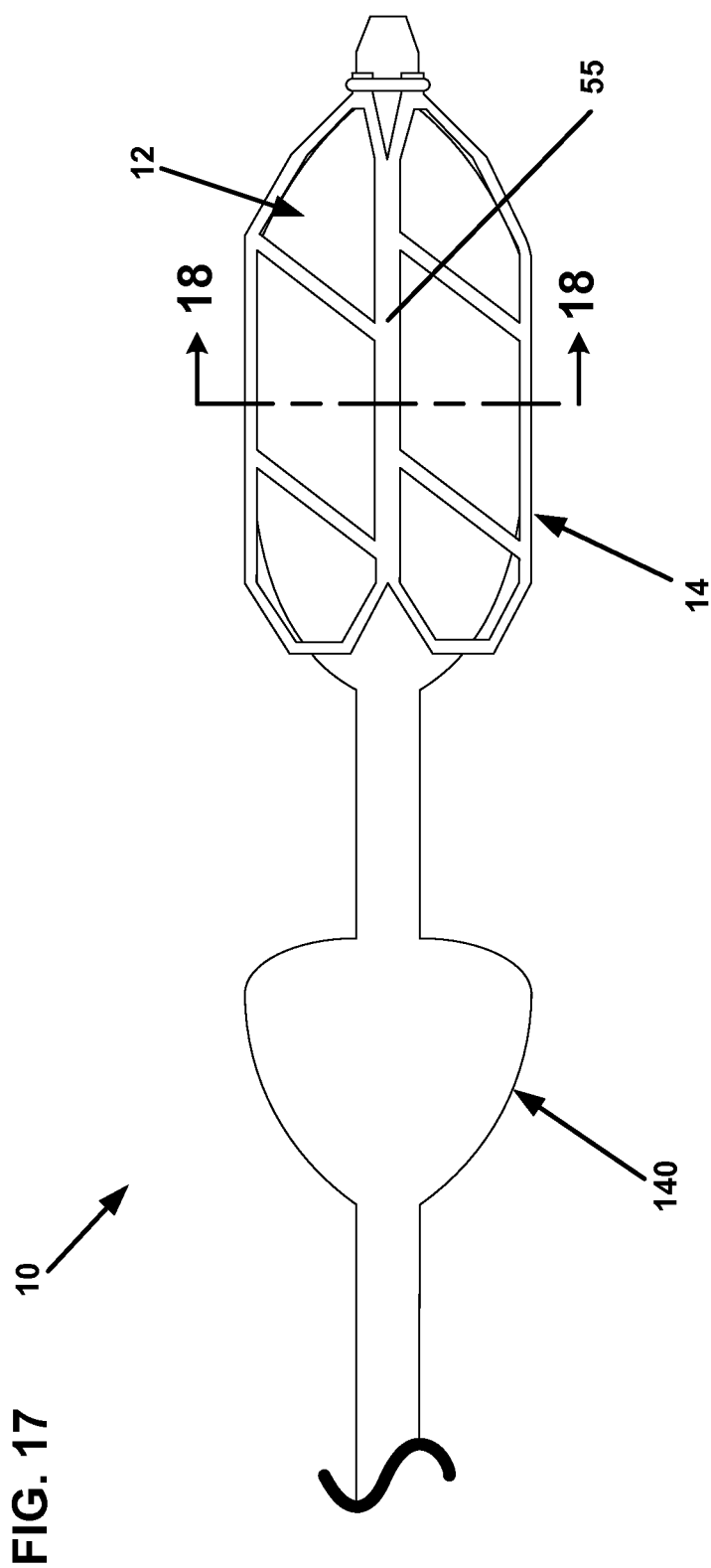
FIG. 17 is an alternate cross-sectional view of the catheter assembly disposed in the guide tube.
Figure 18:
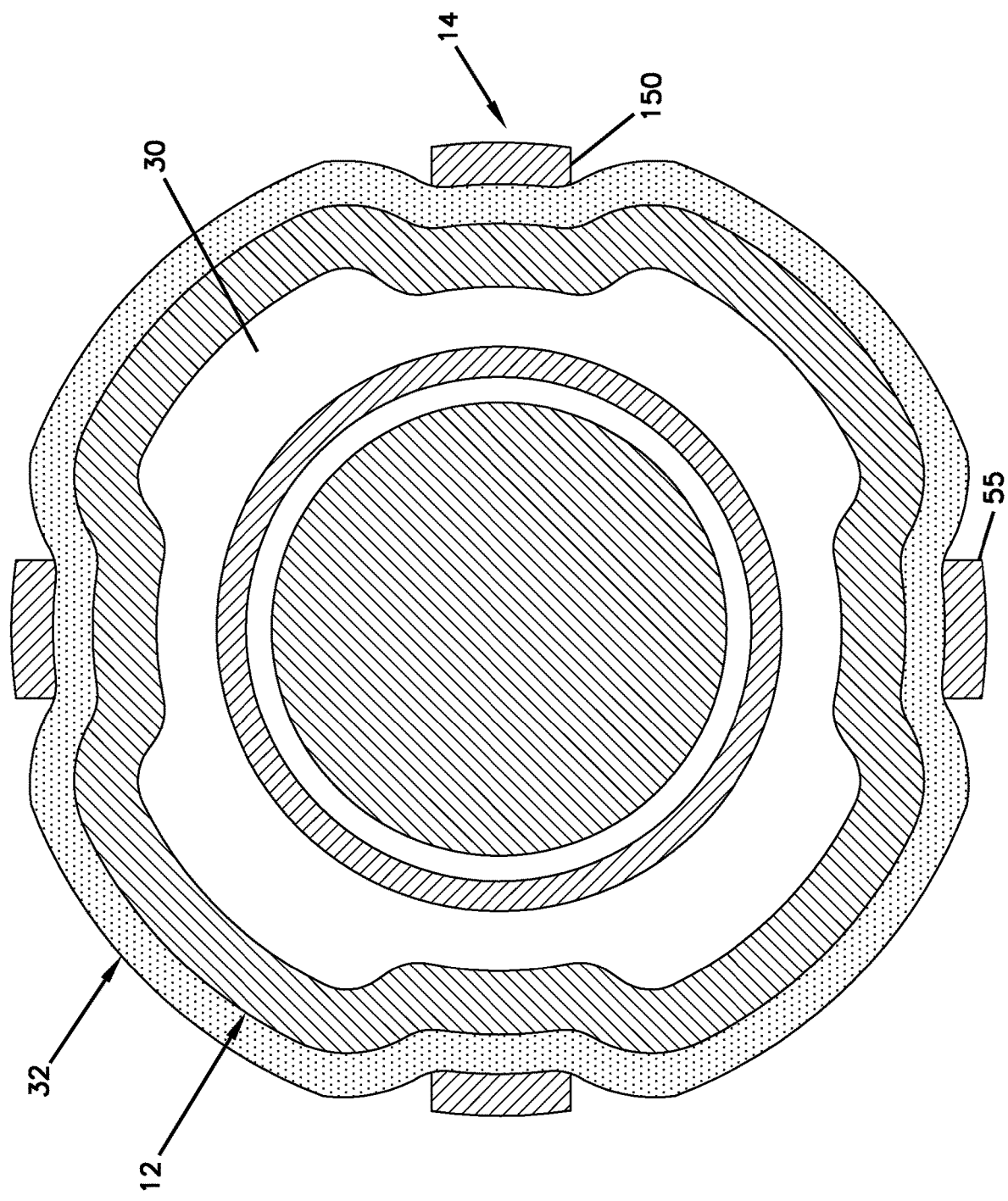
FIG. 18 is an alternate cross-sectional view of the catheter assembly disposed in the guide tube.

Referring now to FIGS. 17 and 18, the use of the catheter assembly 10 will be described. When the catheter assembly 10 is positioned at the target site in the body of the patient, fluid is communicated to the lumen 30 of the expandable and collapsible structure 12 so that the expandable and collapsible structure 12 expands to the dilated state. The pressure of the fluid creates a force that acts against the inner surface 24 of the expandable and collapsible structure 12 causing dilation of the expandable and collapsible structure 12. In one embodiment, the fluid pressure required to expand the expandable and collapsible structure 12 to the dilated state is less than or equal to about 15 atmospheres of pressure. In one embodiment, the fluid pressure required to expand the expandable and collapsible structure 12 to the dilated state is less than or equal to about 10 atmospheres of pressure. In another embodiment, the fluid pressure required to expand the expandable and collapsible structure 12 to the dilated state is in a range of about 5 to 15 atmospheres of pressure. In another embodiment, the fluid pressure required to expand the expandable and collapsible structure 12 to the dilated state is in a range of about 7 to 10 atmospheres of pressure.

In the depicted embodiment of FIG. 17, the second expandable and collapsible structure 140 is also expanded to a dilated state. In one embodiment, the second expandable and collapsible structure 140 is expanded prior to the expansion of the expandable and collapsible structure 12. In one embodiment, the fluid pressure required to expand the expandable and collapsible structure 12 to the dilated state is less than or equal to about 5 atmospheres of pressure. In one embodiment, the fluid pressure required to expand the expandable and collapsible structure 12 to the dilated state is less than or equal to about 3 atmospheres of pressure. In another embodiment, the fluid pressure required to expand the expandable and collapsible structure 12 to the dilated state is in a range of about 1 to 5 atmospheres of pressure. In another embodiment, the fluid pressure required to expand the expandable and collapsible structure 12 to the dilated state is in a range of about 2 to 3 atmospheres of pressure.

The force of the fluid against the inner surface 24 of the expandable and collapsible structure 12 acts against the interior surface 56 of the sleeve 14 and causes the sleeve 14 to expand radially outward to the enlarged state. As the sleeve 14 is expanded, the area of the openings 150 at the exterior surface 55 of the sleeve 14 increases. This increase in area allows for a greater amount of the coating 32 to be in contact with the target site in the body of the patient.

As best shown in FIG. 18, with the expandable and collapsible structure 12 and the sleeve 14 expanded, the coating 32 extends through the openings 150 in the sleeve 14. In the depicted embodiment, the coating 32 extends past the exterior surface 55 of the sleeve 14. This extension of the coating 32 past the exterior surface 55 of the sleeve 14 allows the coating 32 to contact tissue at or surrounding the target site of the body of the patient. With the coating 32 in contact with tissue at or surrounding the target site of the body of the patient, the bioactive agent is delivered to the tissue at or surrounding the target site.

After at least a portion of the bioactive agent of the coating 32 has been delivered, the fluid in the lumen 30 of the expandable and collapsible structure 12 is drained. With the fluid in the lumen 30 removed, the force acting against the interior surface 56 of the sleeve 14 is removed. As the original shape of the shape memory alloy of the sleeve 14 is the compressed state, the sleeve 14 naturally constricts to the compressed state when the fluid in the lumen 30 of the expandable and collapsible structure 12 drained.

The temperature of the sleeve 14 may need to be regulated before the sleeve 14 will naturally constrict. In one embodiment, the temperature of the sleeve 14 can be regulated by routing warm fluid through the lumen 30 of the expandable and collapsible structure 12.

As the sleeve 14 constricts to the compressed state, the expandable and collapsible structure 12 contracts to the contracted state. Once the expandable and collapsible structure 12 and the sleeve 14 are in the contracted and compressed states, respectively, the catheter assembly 10 is removed from the vasculature of the body of the patient through the guide tube 154 (shown in FIG. 14) and withdrawn from the patient.

Various modifications and alterations of this disclosure will become apparent to those skilled in the art without departing from the scope and spirit of this disclosure, and it should be understood that the scope of this disclosure is not to be unduly limited to the illustrative embodiments set forth herein.

What is claimed is:

1. A catheter assembly comprising: an expandable and collapsible structure having an outer surface, the expandable and collapsible structure being adapted to expand between a contracted state and a dilated state; a coating disposed on the outer surface of the expandable and collapsible structure, the coating including a bioactive agent; a sleeve disposed over the coating, a material of the sleeve including nitinol, the sleeve being adapted to expand between a compressed state and an enlarged state in response to a force acting on an interior surface of the sleeve, and to return to the compressed state from the enlarged state when the force is removed, wherein the sleeve is adapted to protect the coating in the compressed state and during expansion of the expandable and collapsible structure, the sleeve including: a body having an interior surface and an exterior surface, the interior surface defining a bore in which the expandable and collapsible structure is disposed; the body defining a plurality of openings that extend through the interior and exterior surfaces, wherein the body of the sleeve includes a plurality of rails that extends between a first end of the body and an oppositely disposed second end of the body, and wherein the rails have undulations adapted to decrease as the sleeve expands to the enlarged state.

2. The catheter assembly of claim 1 wherein the sleeve reduces loss of coating and bioactive agent from abrasion and frictional forces during transit of the assembly to a lesion site.

3. A method for delivering a bioactive agent, to a lesion site, comprising moving the catheter assembly of claim 1 in a blood vessel to a lesion site, wherein the sleeve reduces loss of coating and bioactive agent from abrasion and frictional forces during transit of the assembly to the lesion site, and expanding the expandable and collapsible structure so the sleeve expands to the enlarged state and bioactive agent is delivered to the lesion site.

* * * * *